US010912892B2

(12) United States Patent
Edwards

(10) Patent No.: US 10,912,892 B2
(45) Date of Patent: Feb. 9, 2021

(54) SUBSTANCE DELIVERY APPARATUS, SUBSTANCE DELIVERY SYSTEM AND METHOD OF SUBSTANCE DELIVERY

(71) Applicant: Automed Patent Holdco, LLC, Loveland, CO (US)

(72) Inventor: David Royce Edwards, New Lambton (AU)

(73) Assignee: Automed Patent Holdco, LLC, Loveland, CO (US)

( * ) Notice: Subject to any disclaimer, the term of this patent is extended or adjusted under 35 U.S.C. 154(b) by 703 days.

(21) Appl. No.: 15/463,098

(22) Filed: Mar. 20, 2017

(65) Prior Publication Data
US 2017/0197037 A1    Jul. 13, 2017

Related U.S. Application Data

(63) Continuation of application No. 14/758,418, filed as application No. PCT/AU2014/000014 on Jan. 10, 2014, now abandoned.

(30) Foreign Application Priority Data

Jan. 13, 2013   (AU) ................................ 2013900096

(51) Int. Cl.
*A61M 5/315*    (2006.01)
*A61M 5/20*    (2006.01)
(Continued)

(52) U.S. Cl.
CPC ........... *A61M 5/31546* (2013.01); *A61D 7/00* (2013.01); *A61M 5/20* (2013.01); *A61M 5/204* (2013.01);
(Continued)

(58) Field of Classification Search
CPC ............ A61M 5/31546; A61M 5/2053; A61M 11/007; A61D 7/00
See application file for complete search history.

(56) References Cited

U.S. PATENT DOCUMENTS 5,560,317 A    10/1996  Bunyan et al.
5,997,500 A    12/1999  Cook et al.
(Continued)

FOREIGN PATENT DOCUMENTS

CA    2267812 A1    10/2000

OTHER PUBLICATIONS

International Preliminary Report on Patentabitlity dated Jan. 10, 2014 for International Application No. PCT/AU2014/000014 (7 Pages).

(Continued)

*Primary Examiner* — Rebecca E Eisenberg
*Assistant Examiner* — John A Doubrava
(74) *Attorney, Agent, or Firm* — BlueIron, LLC; Russell Krajec

(57) ABSTRACT

An apparatus for discharging a dose of a fluid substance to an animal, the apparatus including: a delivery assembly adapted to discharge the dose of the substance to the animal; and a control system operatively associated with the delivery assembly so as to selectively operate the delivery assembly, wherein the control system is adapted to measure the discharge of the fluid substance from the delivery assembly such that the dose is discharged when the delivery assembly is operated.

13 Claims, 16 Drawing Sheets

(51) Int. Cl.
*A61D 7/00* (2006.01)
*A61M 11/00* (2006.01)
*A61M 5/32* (2006.01)
*A61M 5/172* (2006.01)

(52) U.S. Cl.
CPC ...... *A61M 5/2053* (2013.01); *A61M 5/31565* (2013.01); *A61M 5/31566* (2013.01); *A61M 5/31576* (2013.01); *A61M 5/32* (2013.01); *A61M 11/007* (2014.02); *A61M 5/172* (2013.01); *A61M 2005/2026* (2013.01); *A61M 2205/33* (2013.01); *A61M 2205/3306* (2013.01); *A61M 2205/3327* (2013.01); *A61M 2205/3576* (2013.01); *A61M 2205/50* (2013.01); *A61M 2205/502* (2013.01); *A61M 2205/52* (2013.01); *A61M 2205/6018* (2013.01); *A61M 2205/6063* (2013.01); *A61M 2250/00* (2013.01)

(56) References Cited

U.S. PATENT DOCUMENTS

| | | | |
|---|---|---|---|
| 6,558,352 B1* | 5/2003 | Hogan | A61D 7/00 600/432 |
| 7,056,307 B2 | 6/2006 | Smith et al. | |
| 2002/0107501 A1 | 8/2002 | Smith et al. | |
| 2005/0171476 A1* | 8/2005 | Judson | A61M 5/20 604/131 |
| 2010/0016796 A1* | 1/2010 | Derichs | A61D 7/00 604/135 |
| 2010/0256554 A1 | 10/2010 | Discher, Jr. et al. | |
| 2011/0224613 A1* | 9/2011 | D'Antonio | A61M 5/204 604/131 |

OTHER PUBLICATIONS

International Search Report dated Jun. 2, 2014 for International Application No. PCT/AU2014/000014 (6 Pages).

* cited by examiner

SUBSTANCE DELIVERY APPARATUS, SUBSTANCE DELIVERY SYSTEM AND METHOD OF SUBSTANCE DELIVERY

TECHNICAL FIELD

The invention relates to a substance delivery apparatus, a system including an apparatus for substance delivery and a method of substance delivery.

BACKGROUND

Animals are often required to be administered a substance such as a medication. In the livestock industry there are typically large numbers of animals that require such medication.

Medication is typically administered to an animal with a dose rate manually determined from animal parameters such as weight, breed, and age. In most cases, the dose rate may be calculated in millilitres of medication per kg of animal weight (ml/kg). Accordingly, to accurately medicate an animal it is desirable to know the weight of the animal.

One of the current industry practices is to weight a sample of the animals or weight all of the animals within a group often referred to in the industry as a herd, flock, or mob. The weight of the heaviest animal is recorded and the medication dose rate is set to the dose required for the heaviest animal in the group. Each animal within the group is then administered the dose rate associated with the heaviest animal.

The process of medication typically includes a medication device such as a syringe or drenching unit from which the dose of medication is manually administered to the animal. This manual administration typically includes hand actuation or pumping of the medication device to deliver the medication to the animal.

In relation to medication records, the current industry practice typically does not include keeping detailed records for the medication administered to a particular animal. Rather, the records typically only include what medication was used and when it was used.

A problem with the current practice is that the age, type and weight of the animals within the group may vary and as such some animals within the group may be overmedicated. This may cause health issues with the animal such as medication resistance and also result in an increased cost of medication.

Another problem with the current practice is that there is no accurate, reliable or fast way of administering and recording of the medication administered to a particular animal or group of animals.

The invention provided herein seeks to address one of more of the problems described above or at least provide a useful alternative.

SUMMARY

In accordance with a first aspect there is provided, an apparatus for discharging a dose of a fluid substance to an animal, the apparatus including: a delivery assembly adapted to discharge the dose of the substance to the animal; and a control system operatively associated with the delivery assembly so as to selectively operate the delivery assembly, wherein the control system is adapted to measure the discharge of the fluid substance from the delivery assembly such that the dose is discharged when the delivery assembly is operated.

In an aspect, the control system includes a sensor configured to measure the discharge of the fluid substance from the delivery assembly.

In another aspect, the delivery assembly includes a substance reservoir in which the fluid substance is containable and drive arrangement configured to move the substance reservoir between an expanded condition and a contracted condition.

In another aspect, the drive arrangement includes a plunger receivable by the substance reservoir.

In another aspect, the sensor is arranged to measure the movement of the plunger.

In another aspect, the plunger includes a first piston received within the substance reservoir and a rod coupled to the first piston.

In another aspect, the first piston is moveable between a first position in which the substance reservoir in the expanded state and a second position in which the substance reservoir is in the contracted state.

In another aspect, the sensor is a linear position sensor and the rod includes a sensor readable section configured such that the liner sensor is able to determine the position of the rod relative to the sensor.

In another aspect, the drive arrangement includes a drive reservoir and the plunger includes second piston received by the drive cylinder, the second piston being connected to an opposing end of the rod relative to the first piston.

In another aspect, the drive arrangement includes a biasing means configured to urge the first piston toward the first position in which the substance reservoir is in the expanded state.

In another aspect, the biasing means is a spring concentrically mounted on the rod.

In another aspect, the rod is hollow rod so as to allow passage of the fluid substance from an inlet to the substance reservoir.

In another aspect, the delivery assembly further includes a delivery conduit which is slidably received by the hollow rod.

In another aspect, a seal is provided between the delivery conduit and hollow rod.

In another aspect, the control system includes a pneumatic control valve in communication with the drive arrangement, the pneumatic control valve being operable so as to selectively introduce pressurised gas into the drive reservoir.

In another aspect, the pneumatic control valve is connectable to a pneumatic system, the pneumatic system being adapted to provide the pressurised gas.

In another aspect, the pneumatic system includes at least one of a pressuring vessel and a pneumatic fill nozzle pneumatically connected to the pneumatic control valve.

In another aspect, the control system includes a hydraulic control valve adapted to selectively control flow into and out of the substance reservoir.

In another aspect, the apparatus includes in an information input device operatively associated with the control system, the information input device being configured to provide animal information, and wherein the control system includes a processor which is configured to determine the predetermined quantity of the substance based on the animal information.

In another aspect, the information input device is provided in the form of an identification device operatively associated with the control system, the identification device being configured to provide identity information for the animal.

In another aspect, the identification device is one of a radio frequency identification device (RFID) and an optical scanner.

In another aspect, the identification device includes an antenna recessed within a body of the apparatus.

In another aspect, the antenna is located toward a forward end of the apparatus.

In another aspect, the control system includes a memory device and a processor.

In another aspect, the control system includes including a communication device for providing a data or electrical link between the apparatus and an external device.

In another aspect, the communication device includes an antenna.

In another aspect, the apparatus includes an actuator operatively associated with the control system.

In another aspect, the actuator is one of an external input, button, a trigger and an electrical signal.

In another aspect, the actuator is hand operable trigger.

In another aspect, the apparatus includes a handle.

In another aspect, the apparatus is gun shaped with a barrel section supported by the handle, the barrel section substantially housing the substance delivery assembly.

In another aspect, the apparatus further includes a display connected to the control system.

In another aspect, the display includes at least one of indication light or a screen.

In another aspect, the fluid substance is at least one of a medication and a vitamin.

In another aspect, the apparatus includes an applicator adapted to deliver the substance to the animal.

In another aspect, the applicator is one of a needle, spray, nozzle or drench.

In accordance with a second aspect there is provided, a system for delivering a dose of a substance to an animal, the system including: a delivery assembly configured to deliver a dose of the substance to the animal; a controller operatively associated with the delivery assembly; and an input device in communication with the controller for providing animal information to the controller; wherein the controller is configured to process the animal information and output a dose rate signal to the delivery assembly enabling the delivery assembly to deliver the dose of the substance to the animal.

In an aspect, the input device is provided in the form of an identification device configured to provide the animal information including animal identification information, and wherein the controller is configured determine the dose rate signal based on the animal identification information.

In another aspect, the system further includes a sensor operatively associated with the delivery assembly, the sensor providing a measured dose rate signal to the controller, the controller being configured to compare the dose rate signal to the measured dose rate signal to determine when the delivery assembly has delivered the dose.

In another aspect, the system includes at least one control valve associated with the delivery assembly, wherein the control valve is in communication with the controller which is configured to open and close the control valve to control the delivery of the dose.

In another aspect, the delivery assembly includes a substance reservoir moveable between a filled condition and an emptied condition.

In another aspect, the delivery assembly further includes a drive arrangement operatively associated with the controller, the drive arrangement being configured to move the substance reservoir between the filled and the emptied conditions to deliver the dose of the substance to the animal.

In another aspect, the controller includes a processor and a memory device configured to record the identity signal and the delivered dose rate signal.

In another aspect, the animal information includes at least one of animal identification, animal weight and animal age.

In accordance with a third aspect there is provided, a method for delivering a dose of a substance to an animal using a substance delivery system including a delivery assembly operatively associated with a controller, wherein the method includes the steps of: Receiving animal information; Processing, in a controller of the system, the animal information to provide a determined dose of the substance to be administered to the animal; and Activating the delivery assembly such that delivery system discharges the determined dose of the substance to the animal.

In an aspect, the animal infot nation includes at least one of animal weight data, animal identification data and animal age data.

In another aspect, the method includes the step of: identifying the animal using an identification device to provide the animal information including the animal identification data.

In another aspect, the step of identifying the animal includes communicating the identification device with an associated identifying device located on or inside the animal.

In another aspect, the method includes the step of: recording the determined dose in a memory device in communication with the controller.

In another aspect, the step of processing the animal information includes the controller accessing information stored on the memory device.

In another aspect, the information stored on the memory device includes at least one of further animal information and medication information.

In another aspect, the further animal information includes data in relation to the animal identification, weight, type and age and the medication information includes medication type and dose rate information.

In another aspect, the step of processing the animal information includes calculating the dose rate by using a dose rate algorithm.

In another aspect, the dose rate algorithm is executed by a processor associated with the controller and includes the steps of: Accessing the animal information and the medication information to determine the weight and the medication rate for the animal; Determining the dose rate based on the weight and medication rate for the animal; Providing a dose rate signal to the delivery assembly.

In another aspect, the dose rate signal includes a calculated distance related to a volume of substance discharged from the delivery assembly such that when the delivery assembly moves the distance, the volume of substance discharged.

In another aspect, the delivery assembly includes a sensor and a drive arrangement, wherein the method includes the steps of: activating the drive arrangement to move the distance thereby delivering the volume of the substance; and measuring the movement of the drive arrangement with the sensor, the sensor providing a measurement distance signal to the controller.

In another aspect, the method includes the step of ceasing substance delivery when the measured distance is substantially equal to the calculated distance.

In another aspect, the method includes the step of activating the drive arrangement by operating a pneumatic control valve so as to allow a pressurised gas to communicate with a drive cylinder of the drive arrangement.

In accordance with a fourth aspect there is provided, an apparatus for communicating a fluid substance with an animal, the apparatus including: an fluid transmission assembly adapted to communicate a quantity of the substance with the animal; and a control system operatively associated with the delivery system so as to selectively operate the fluid transmission assembly, wherein the fluid transmission assembly includes a sensor configured to measure the communication of the fluid substance such that the quantity of the substance is communicated between the apparatus and the animal when the fluid transmission assembly is operated.

In accordance with a fifth aspect there is provided, a system for communicating a quantity of a substance to an animal, the system including: a fluid communication assembly configured to communicate a quantity of the substance between the animal and the system; an identification device for providing an animal identity signal; and a controller operatively associated with the fluid communication assembly and the identification device, wherein the controller is configured to receive the identity signal, processes information associated with the identity signal and output a quantity rate signal to the fluid communication enabling the fluid communication to communicate the quantity of the substance to the animal.

BRIEF DESCRIPTION OF THE FIGURES

The invention is described, by way of non-limiting example only, by reference to the accompanying figures, in which.

DETAILED DESCRIPTION

Figure 1:
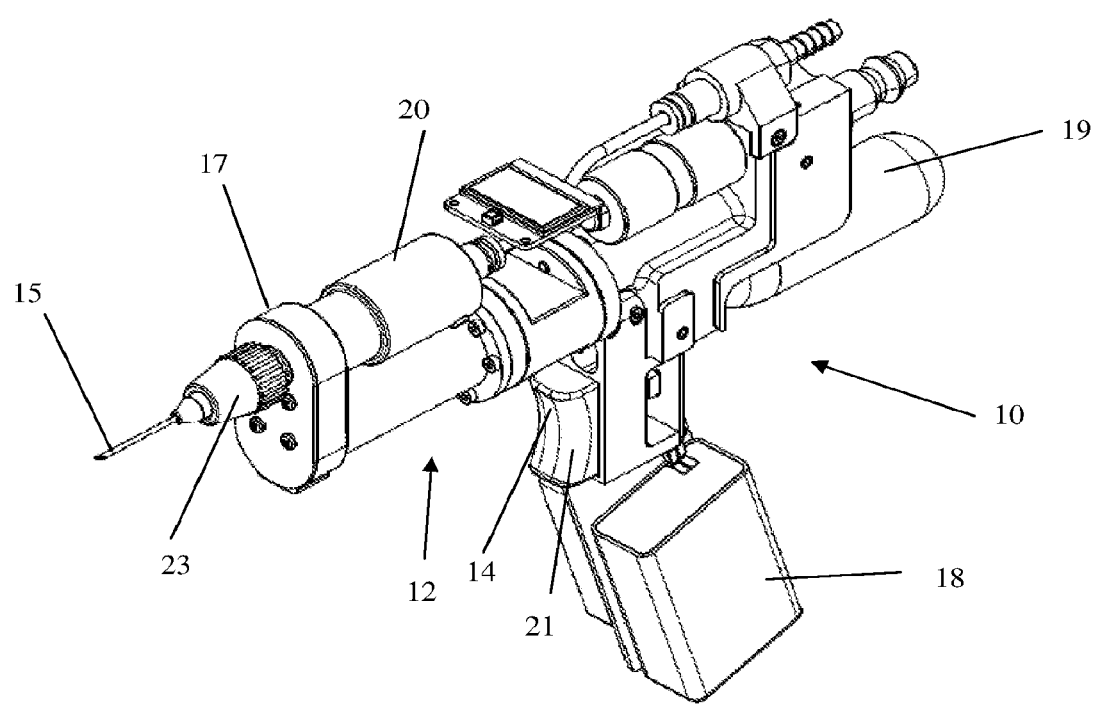
FIG. 1 is a perspective view illustrating an apparatus for administering medication to an animal with an needle type applicator tip fitted.

Referring to FIG. 1, there is shown an apparatus 10 for communicating, more particularly administering a substance such as medication to an animal. The apparatus 10 includes a fluid communication or transmission assembly provided in this example as a delivery assembly 12. The delivery assembly 12 is adapted to communicate or deliver a select quantity of fluid, in this example a pre-determined quantity or dose of the medication to the animal. The apparatus 10 includes an actuator 14 which is configured to selectively operate the delivery assembly 12 via a control system 100 which is further described below.

The apparatus 10 is preferably hand held and includes a gun shaped body 16 which houses and supports the delivery assembly 12 and the actuator 14, respectively. The body 16 includes handle 18 portion which supports a barrel or main portion 20. The actuator 14 is provided in the form of a trigger 21 is located on or within the handle portion 21 and the delivery assembly 12 is substantially located on or within the main portion 20.

The body 16 includes a delivery or front end 17 and a rear end 19. An applicator 23 for delivering or receiving fluid or medication to and from and animal such as a needle or drench is located at the front end 17 of the apparatus 10. The body 16 typically includes a housing or casing (not shown) which is adapted to shield and seal the components of the apparatus 10 therein.

The apparatus 10 also includes a display 29 for displaying status and animal information and a LED light 27 which are used to display, confirm or select various modes of operations and statuses of the apparatus 10. The display 29 may form part of the control system 100 and allow a user to provide input to the control system 100.

Figure 2:
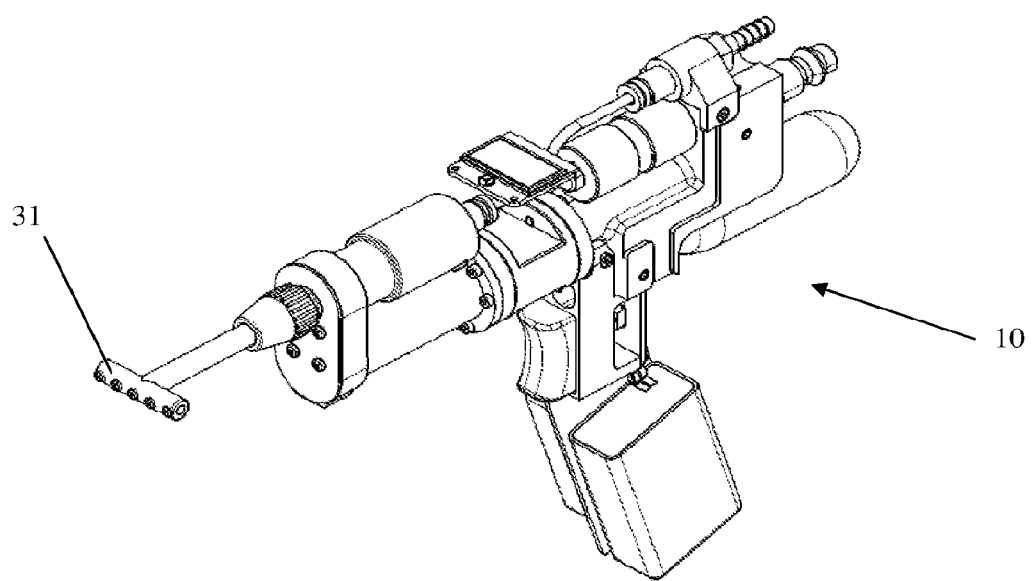
FIG. 2 is a perspective view illustrating the apparatus for administering medication to the animal with spray type applicator tip fitted.
Figure 3:
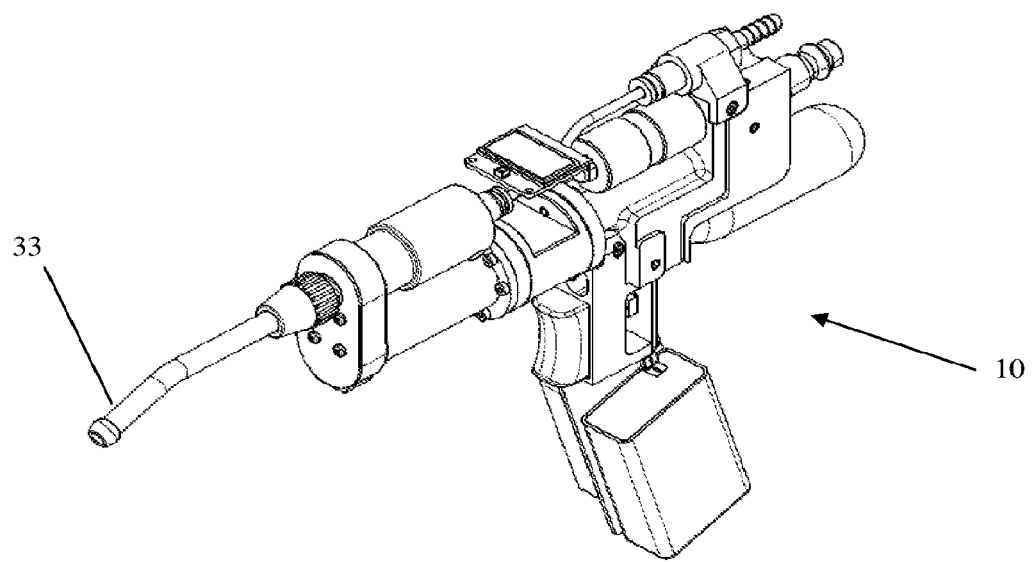
FIG. 3 is a perspective view illustrating the apparatus for administering medication to the animal with a drenching type applicator tip fitted.

In this example, the applicator 23 includes a needle 15 fitted to a threaded coupling 13 of the delivery manifold 36. However, as is shown in FIGS. 2 and 3, the applicator 23 may also be a spray fitting 31 or a drench fitting 33.

Figure 4A:
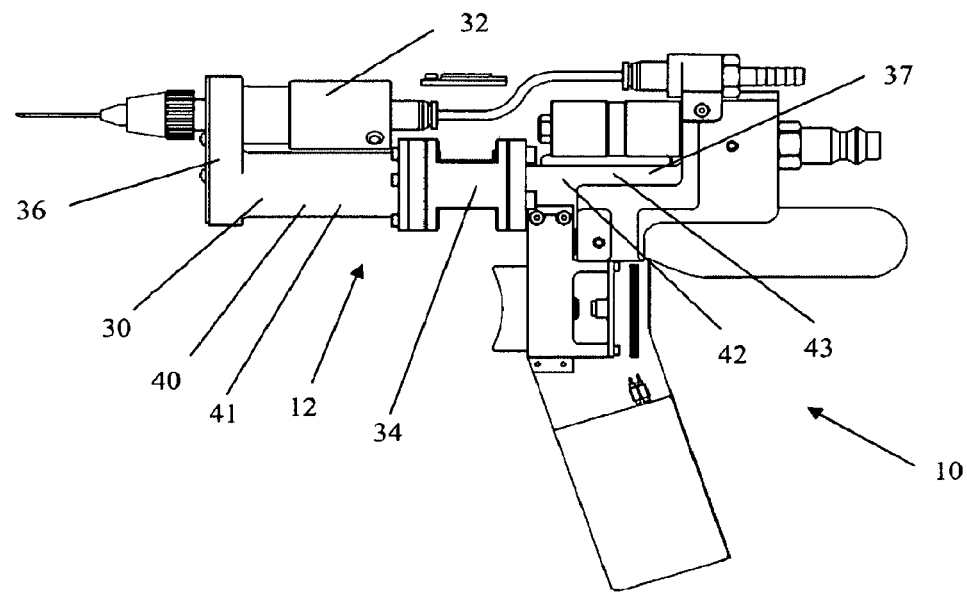
FIG. 4a is a side view illustrating the apparatus.

Referring additionally to FIG. 4a, the delivery assembly 12 includes a substance reservoir arrangement 30 and a drive arrangement 37 arranged to moved the substance reservoir arrangement 30 between an emptied or contracted condition and a filled or expended condition. The substance reservoir arrangement 30 includes a medication cylinder 40 which provides a medication reservoir 41 for the temporary storage of medication.

The drive arrangement 37 is operatively associated with the medication cylinder 40, in particular, the medication reservoir 41 to draw medication into the reservoir 41 and urge medication out of the reservoir 41. The drive arrangement 37 includes a drive cylinder 42 which provides a drive reservoir 43. The drive cylinder 42 and medication cylinder 40 coupled to or linked to one another by a plunger 37 (shown in FIGS. 5a to 5c) for likewise control and actuation.

The delivery assembly 12 further includes delivery manifold 36 and a hydraulic or medication substance control valve 32. The delivery manifold 36 is located between the medication cylinder 40, the control valve 32 and the applicator 23. The manifold 36 includes conduits or ports (shown in more detail FIGS. 7a and 7b) through which fluid or medication is able to flow thereby operatively coupling the medication cylinder 40, the control valve 32 and the applicator 23.

Figure 4B:
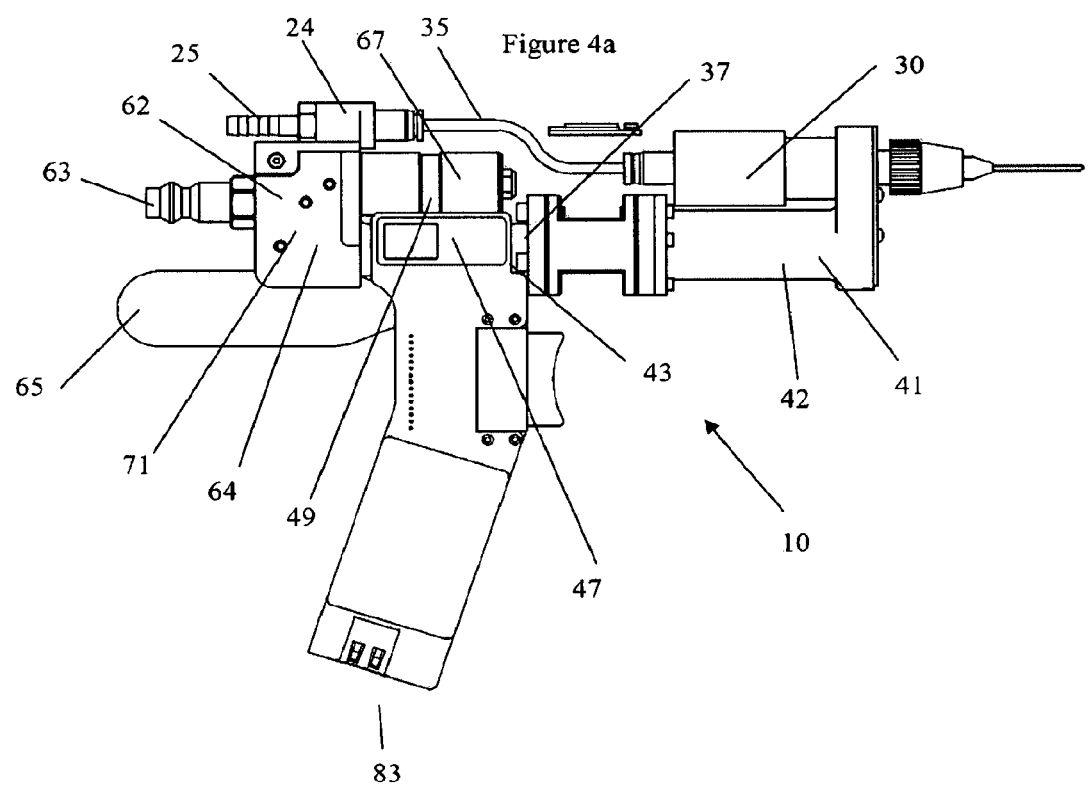
FIG. 4B is an opposing side view illustrating the apparatus.

Referring now to FIG. 4b, the apparatus 10 includes a pneumatic power system or energy unit 62 coupled to the drive arrangement 37. The power unit 62 includes a pneumatic system 64 including a pressurised canister or vessel 65 for containing a pressurised gas, such as carbon dioxide, $CO_2$ and a pneumatic manifold 71. The control system 100 include a pneumatic control valve 67 is located within or in communication with the pneumatic manifold 71. The pneumatic control valve 67 is used to control the flow of pressurised gas between the pneumatic power system 62 and the drive arrangement 37.

More specifically, the drive cylinder 42 is coupled to the pneumatic system 64 via the pneumatic control valve 67 so as to provide a controlled delivery and release of pressure to the drive cylinder 40, expanding and contracting the drive reservoir 43. The pneumatic power unit 62 powers or provides an energised force to move the drive arrangement 37 thereby enabling movement fluid substances such as medication into and out of the medication reservoir 41. Together the drive arrangement 37, pneumatic power unit 62 and control system 100 provide a controllable pneumatic drive system 49 for the controlled release and introduction of fluid substances, in this example medication, into and out of the medication storage and delivery arrangement 30.

The power unit 64 also includes a pneumatic fill nozzle or coupling 63 which may be fluidly coupled to an external source of pressurised gas such as a LPG gas bottle or Oxygen bottle. Accordingly, the device can either use the pressurised vessel 65 or an external source of pressurised gas supply via the coupling 63.

A fluid substance such as medication may be introduced into the apparatus via a medication fill tube 35 connected to the fluid control valve 32. The tube 35 is connected to a ribbed nozzle 25 via a support housing 24 connected to and located above the pneumatic manifold 71.

Figure 4C:
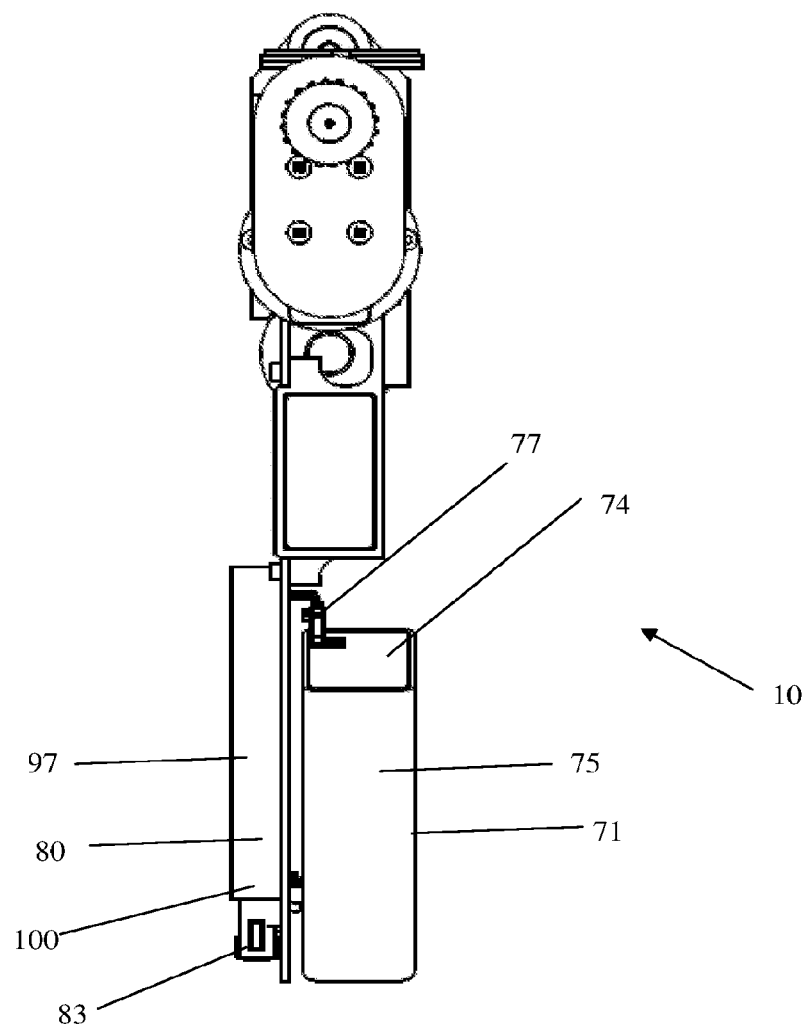
FIG. 4c is a front view illustrating the apparatus.

Referring to FIG. 4c, the handle 21 of the apparatus 10 provides a first housing 75 for an electrical power source such as a battery pack 74 with terminals 77 and a second housing 97 for a control board 80 which is described in further detail below. The control board 80 supports the components of the control system 100 which is used to control, monitor and record the functions of the apparatus 10. The control system 100 is further described in FIG. 9.

The apparatus 10 may also include a connection system 83 to provide a physical connection between the apparatus 10 and the computer or mobile computing device. The connection system 83 may be any connection suitable for data communication with a computer, or similar external device such as external memory, processing and/or screen. The connection 83 may be a USB connection or the like. The connection system 83 may be used to communicate data to and from the apparatus 10.

The apparatus 10 may also include a wireless communication module or device such as blue tooth or WiFi including an antenna 47 for communication with internal or external devices and systems. The wireless communication module may be used in isolation or in conjunction with the connection 83. The connection 83 and WiFi antenna and associated module, may be broadly considered as input device from which the control system receives information such as animal information from external sources.

Figure 5A:
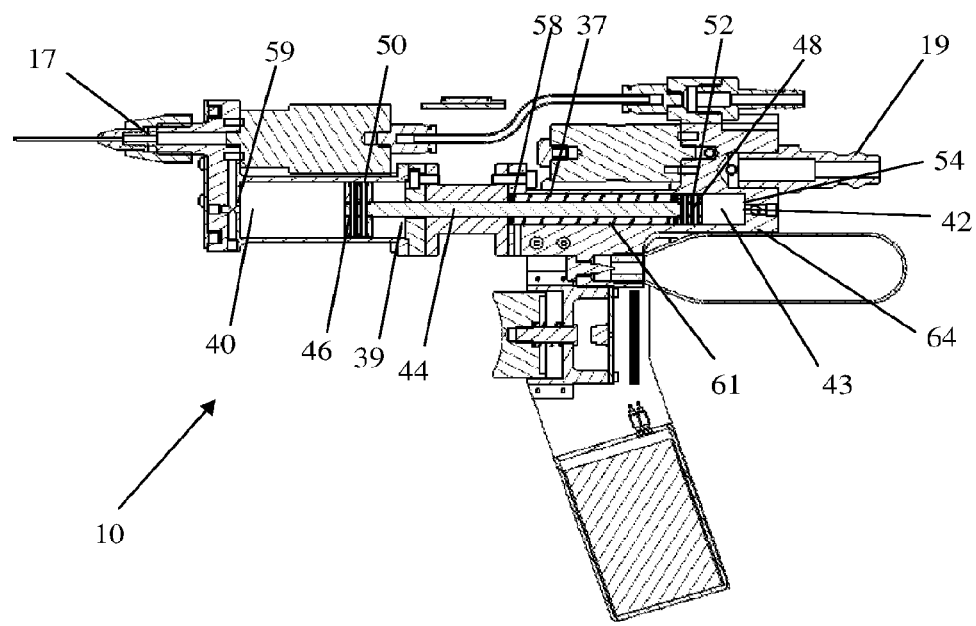
FIG. 5a is a side sectional view illustrating the apparatus.

Referring to FIG. 5a, the plunger 39 of the drive arrangement 37 includes a piston rod 44 spanning between a first or medication piston 46 and a second or drive piston 48. The first or medication piston 46 is located within the medication cylinder 40 and a second or drive piston 48 is located within the drive cylinder 42. Accordingly, the medication cylinder 40 and the drive cylinder 42 are coupled by the plunger 39.

Each of the medication piston 46 and the drive piston 48 are configured to seal with and slidably engage with inner walls of the medication cylinder 40 and the drive cylinder 42, respectively. Preferably, each of the pistons 46, 48 include rubber double flanged cylindrical seals 50, 52 connected to respective ends of the piston rod 44 for sealing with and slidably engage with inner walls of the medication and drive cylinders 40, 42. The seals 50, 52 may be provided in the form of O-rings. It is also noted that the medication cylinder 40 is a larger diameter relative to the drive cylinder 42 and hence the medication piston 46 is a larger diameter relative the drive piston 48.

The piston rod 44 is moveable between a first position, where the piston rod 44 is retracted toward the rear end 19 and a second position wherein the piston rod 44 is extended toward the front end 17. In the first position, the medication reservoir 41 in an expended state and a second position the reservoir 41 is in a contracted state.

The piston rod 44 is biased toward the first position by a biasing means, in this example a spring 61, which is concentrically mounted on the piston rod 44 within the drive cylinder 42. A power unit 64 is coupled to the drive reservoir 43 and functions to provide a pressurised gas, via the control valve 67, to urge or force the piston rod 44 toward the second position. When the pressure is released, the spring 61 urges or forces the piston rod back to or toward the first position.

In more detail, in the first position, the drive reservoir 43 is substantially evacuated and the drive piston 48 is adjacent to or abuts a rear end 54 of the drive cylinder 42. In this position, the medication reservoir 41 is substantially opened and the medication piston 46 is located adjacent to or abuts a rear end 56 of the medication cylinder 40. This allows for the ingress and storage of medication within the medication reservoir 41.

When the piston rod 44 is moved from the first position toward or to the second position, the drive reservoir 43 becomes expanded with the drive piston 48 moving toward a front end 58 of the drive cylinder 42 and the mediation reservoir 41 is reduced or contacts with the medication piston 46 moving toward a front end 59 of the medication cylinder 60. This compresses any medication within the reservoir 41 and allows for the egress of the medication from the reservoir 41.

Figure 5B:
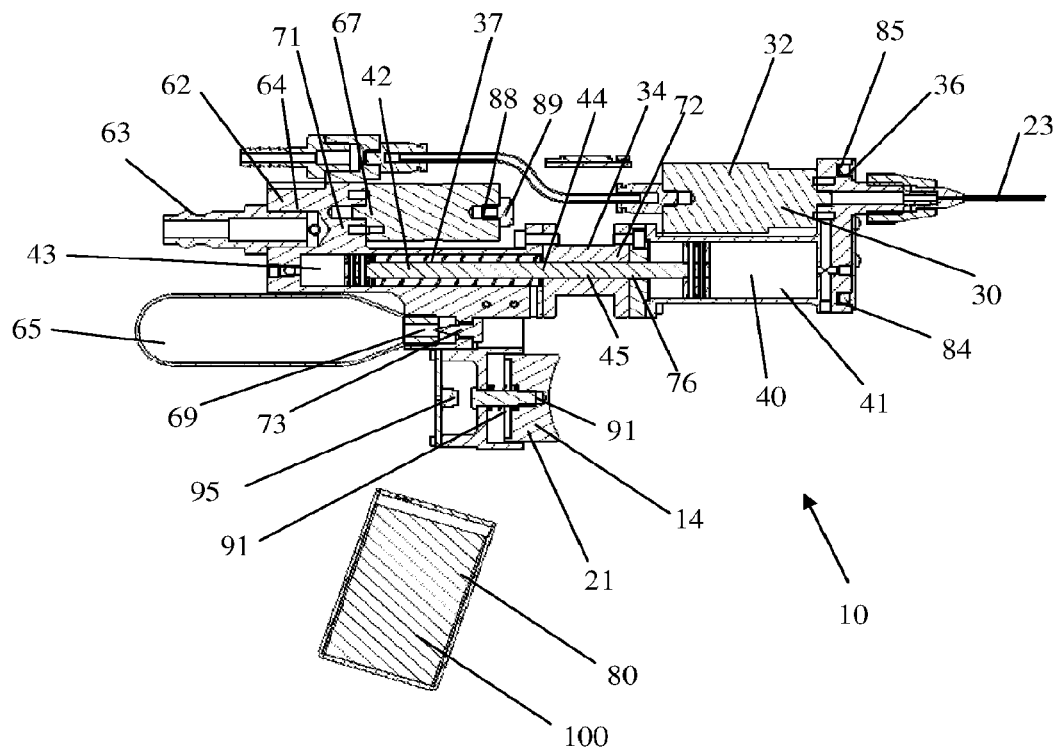
FIG. 5b is an opposing side sectional view illustrating the apparatus.

Referring to FIG. 5b, the measuring unit or sensor 34 is located and abutted between the medication cylinder 40 and the drive cylinder 42. The measuring unit 34 is operatively coupled to or electrically connected to the control board 80. The measuring unit 34 includes a linear sensor, in this example an absolute encoder 72, concentrically mounted on the piston rod 44 with the piston rod 44 passing through a central bore 76 of the encoder 72.

The piston rod 44 includes an encoded or sensor portion 45 which is substantially made from steel, to exploit its soft magnetic characteristics includes absolute code under the surface which is composed of small circumferential grooves. The grooves are filled with non-magnetic material such as hard chrome or copper, depending on the application. The surface is plated with hard chrome and polished to a fine finish. The piston rod 44 may be entirely formed of the encoded or sensor portion 45 or only a select portion of the piston rod 44 may be formed of the encoded portion.

Accordingly, when encoded portion 45 moves through the bore 76 of the encoder 72, the encoder 72 is able to detect the code of the encoded portion and provides a signal to the control system 100 which is proportional to or representative of the absolute position of the piston rod 44 and hence the position of the medication piston 46 and the drive piston 48. Once the position of the medication piston 46 and the drive piston 48 are known, then the volumes of the medication reservoir 41 and the drive reservoir 43 may also be determined. As such, the volumes of medication delivered or received in volume units such as millilitres may be determined and recorded by the control system 100 as is further detailed below.

Accordingly, the measuring sensor unit 34 may be used to determine the amount of medication stored within or delivered or expelled from the medication reservoir 41. In this example, the encoder 72 was selected with an accuracy of ±5 μm. However, other applications may require differing accuracies or arrangements. For example, other distance or measurement sensors may be used such as a laser distance measurement sensor (not shown). If a laser is used then the laser may be positioned behind or axially behind the plunger and a reflection surface may be attached to or located on a rear end of the plunger. The laser which may be fixed to the apparatus would then be able to measure the linear distance between the laser and reflection surface thereby providing a measurement of linear distance moved by the plunger.

The medication control valve 32 is preferably a 3-way sub-miniature solenoid valve and is coupled between the medication storage and drive arrangement 30, the delivery manifold 36 and the medication fill tube 35. The valve 32 is operatively coupled to or electrically connected to the control system 100 which is configured to selectively open or energise and close or de-energised the 3-way valve.

Accordingly, in one mode of operation the valve 32 may direct medication between the medication fill tube 35 into the medication cylinder arrangement 30 via the delivery manifold 36. This mode may be used when drawing or filling the medication reservoir 41. In another mode of operation, the path to the medication fill tube 35 is closed and the valve 32 may direct flow between the medication reservoir 41 to the applicator 23 via the delivery manifold 36. This mode may be used when the medication is being delivered or administered to the animal.

Turning to the pneumatic power unit 62 and the pneumatic system 64 in more detail, the pressurised vessel 65 may be a pre-pressurised canister that screws directly into a threaded socket 69 on the body 16 of the apparatus 10. The socket 69 is connected to the control valve 67 through the manifold 71. The socket 69 includes a gas cylinder pin 73 which is shaped and positioned to piece a cap or seal (not shown) of the pressurised vessel 65 when the pressurised vessel is coupled with, more specifically, screwed into the threaded socket 69.

The pneumatic manifold 71 includes a flow control ball (not shown) that is pushed one way when gas is supplied by the pneumatic nozzle 63 or pushes the other way if air is being supplied by the pressurised vessel 65. Accordingly, the power unit 62, more specifically, the pneumatic system 64 has the ability to automatically switch between local or on board pressurised gas supplied by the vessel 65 or an external source of pressurised gas supplied by the nozzle 63.

Whilst in this example the power unit 62 has been shown to include an on board pressurised gas supplied by the vessel 65 and an external source of pressurised gas supply via the coupling nozzle 63, the power unit 64 may only include one of the vessel 65 or nozzle 63 depending on the application. It is also envisaged that other energy units or power supply configurations to drive arrangement 37 and hence the piston rod 44 could be used such as mechanical or electromechanical systems.

An advantage of the pressurised vessel 65 is that these may be small $CO_2$ cartridges which able to be easily transported, stored and readily purchased. This allows users in remote locations, who may not have access to an external gas supply, to use the apparatus 10. Moreover, the cartridges are able to be quickly and easily changed in the field.

The pneumatic control valve 67 is fluidly coupled between the pressurised vessel 64 or external pressure source and the drive cylinder 42 such that the pneumatic control valve 67 is able to selectively control the flow of the pressurised gas into the drive cylinder 42 and hence the drive reservoir 43. More specifically, the manifold 71 has internal holes or conduits which provide fluid connections between the components of the pneumatic system 64 such as between the pneumatic control valve 67 and the drive cylinder 42.

The pneumatic control valve 67 is coupled to or electrically connected to directly or indirectly via the control system 100 to the actuator 14 in the example the trigger 21. Accordingly, for example, when the trigger 21 is depressed, compressed air from the pressurised vessel 64 is directed through the pneumatic control valve 67 into the drive cylinder 42. This pressurises and expands the drive reservoir 43 which in turn urges the piston rod 44 toward the second position in which medication reservoir 41 is compressed and any medication therein may be urged or directed through the hydraulic control valve 32 into the delivery manifold 36 and ultimately administered to the animal via the applicator 23.

When the required dose rate is reached, the pneumatic control valve 67 shuts off the pressurised air to the drive cylinder 42 and opens a gas release port 88. This allows the spring 61 to return the plunger 39 to the first position. The gas release port 88 is fitted with a silencer 89 to inhibit noise and seal the pneumatic control valve 67 from the external environment.

The power supply 82 is preferably an on board battery pack which is fitted in housing 75. However, the apparatus 10 may also be configured to use an external power supply.

The trigger 21 includes a trigger body 22 slidably connected to the body 16 by a pin 91. A trigger spring 93 is provided between the body 16 and the trigger body 22 to bias the trigger 21 into an outward position in which a trigger button 95, which in this example is a micro-switch is depressed. When the trigger 21 is depressed and moves inwardly to an inward position, the pin 91 engages and depresses the trigger button 95. This activates the apparatus 10 by, for example, sending a signal to the control system 100.

Figure 5C:
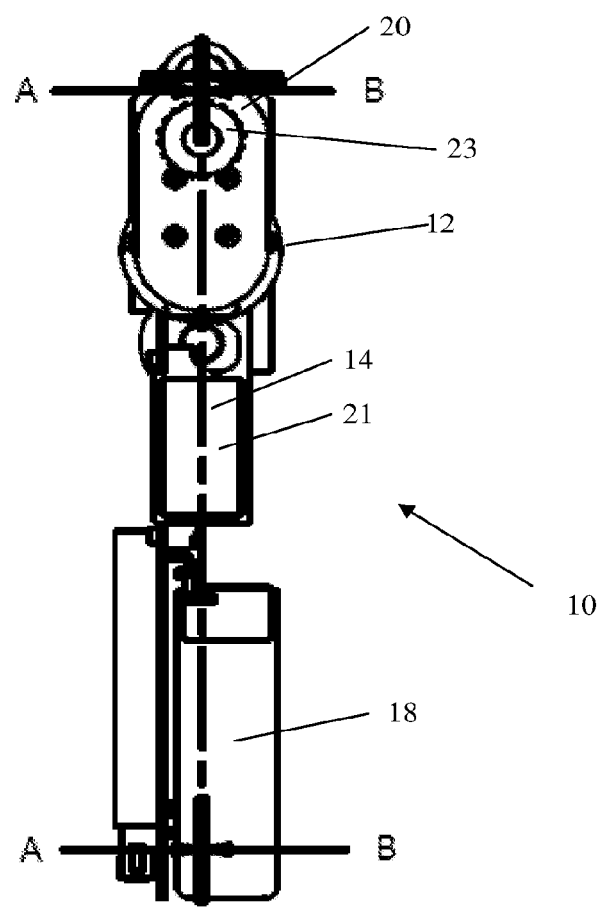
FIG. 5c is a front view illustrating apparatus and showing sections A-A and B-B as are shown in FIGS. 5a and 5b respectively.

Referring to FIGS. 5*b* and 5*c*, the apparatus also include a detection or identification reader device 84 which is provided in this example as Radio Frequency Identification Device (RFID). The detection device 84 is located on the front or application end 17 of the body 16. More specially, the detection device 84 includes an integrally fitted antenna or receiver 85 which is integrally fitted with and recessed in the delivery manifold 36. The reader device 84 is connected to the control system 100 to provide an animal identification signal thereto.

Figure 6A:
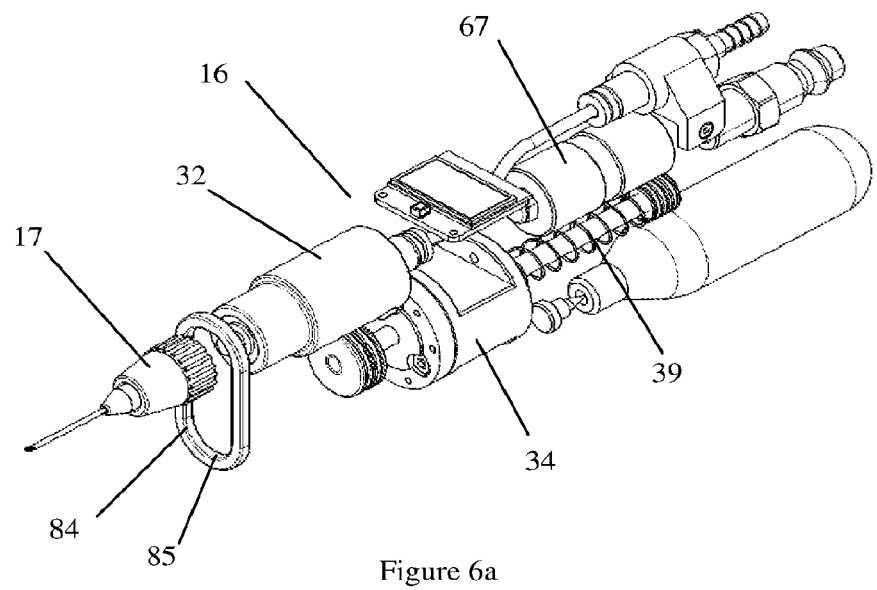
FIG. 6a is a perspective view illustrating parts of the apparatus.
Figure 6B:
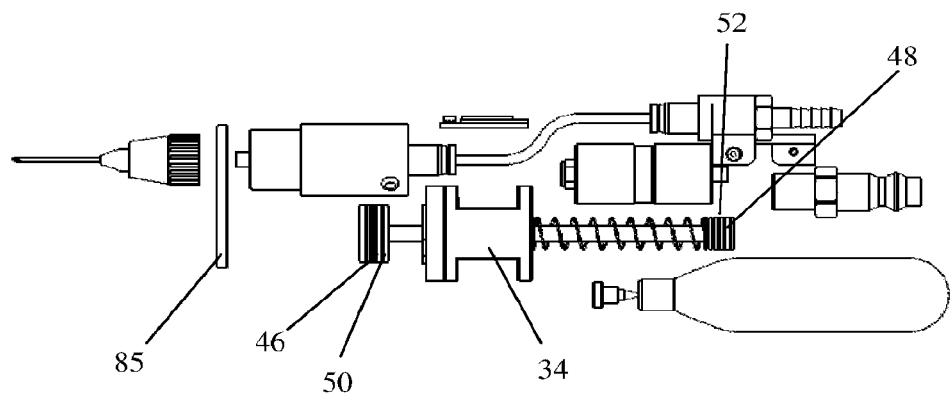
FIG. 6b is a side view illustrating parts of the apparatus.
Figure 6C:
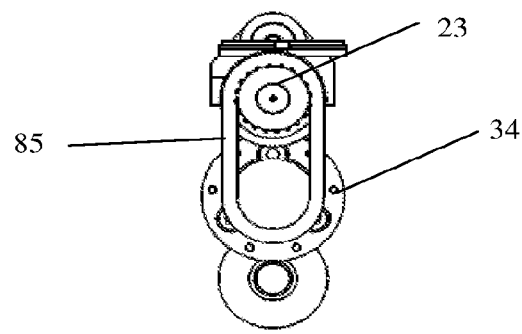
FIG. 6c is a front view illustrating parts of the apparatus.

Referring to FIGS. 6a to 6c, the apparatus 10 is shown with the housing and handle of the body 16 removed as well as the manifold blocks 36 and 71 removed. Accordingly, from this view the layout of some of key operation components such as the hydraulic control valve 32, the measurement sensor 34 and the pneumatic control valve 67 may be more clearly seen.

In particular, from these views, the antenna 85 of the identification device 84 is shown removed from the manifold 36. In this example, the identification device 84 is an RFID reader and the antenna is a circular or an oval shaped cooper wire. The wire is then recessed into the manifold 36 as is described in more detail below with reference to FIGS. 7a and 7b.

The arrangement of the plunger 39 extending through the senor 34 is also shown in more detail. In particular, the spring 61 is shown extending and captured between the sensor 34 and the drive piston 48. The seals 50, 52 of the medication piston 46 and the drive piston 48 are also shown in more detail and each include spaced apart n-rings dimensioned to engage with and seal with the inner walls of the medication cylinder 40 and the drive cylinder 42 respectively.

Figure 7A:
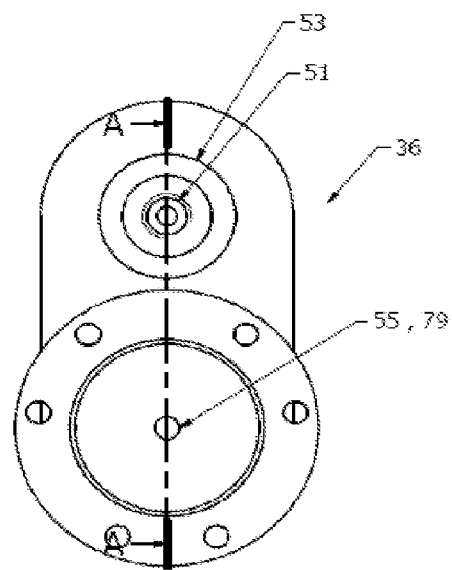
FIG. 7a is a front view illustrating the delivery manifold illustrating section A-A as shown on FIG. 6b.
Figure 7B:
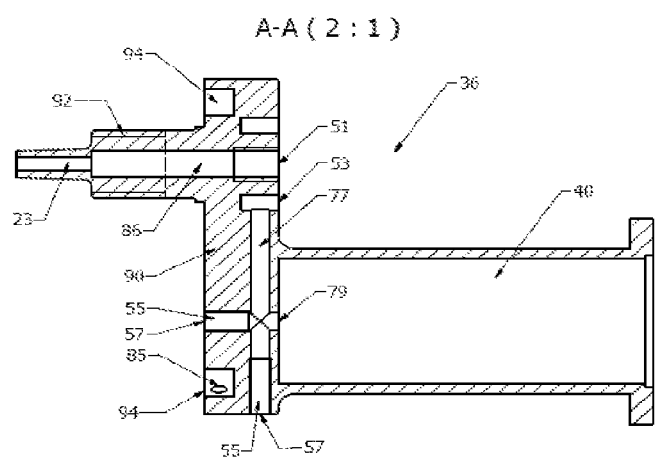
FIG. 7b is a sectional side view of the delivery manifold.

Referring now to FIGS. 7a and 7b, the delivery manifold 36 is shown in more detail. The delivery manifold 36 includes an applicator aperture port or aperture 51 entering into an applicator conduit 86 which provides a fluid coupling between the pneumatic valve 32 (removed in these Figures) and the applicator 23.

The delivery manifold 36 also includes a delivery conduit 77 extending between a first delivery aperture or port 53 and a second delivery aperture or port 79. Accordingly, delivery conduit 77 extends between the pneumatic valve 32 and the medication cylinder 40. The delivery manifold 36 also includes cleaning or flushing ports 55 which are sealed by removable seals in this example grub screws 57.

In this example, the delivery manifold 36 includes a main unity body or block 90 and a protruding section 92 from which the applicator 23 extends. The conduit 86 is located in the protruding section 92 and the conduit 77 is located in the main body 90 and extends perpendicularly relative to the conduit 86.

The medication cylinder 40 extends from the main body 90 and may be formed as integrally with the body 90 with the port 79 aligned with an axis of the cylinder 40. The main unity body or block 90 includes an oval shaped cut out or recess 94 in which an RFID antenna 85 of the identification device 84 is received. The delivery manifold 36 also serves to provide a structural connector between the hydraulic control valve 32, the cylinder 40 and the applicator 23.

Turning now to the flow and delivery of the fluid substance in more detail, by way of example only, the process for medication flow into and out of the apparatus 10 may function as follows:

Medication enters the apparatus via the medication fill tube 35;

The fill tube 35 is connected to a receiving port on the hydraulic control valve 32 and when the valve 32 is configured to open the receiving port, the medication flows through the receiving port to a delivery port 53 of the valve 32;

From the delivery port of the valve 32 the medication then flows into port 53 of the medication delivery manifold 36 and through conduit 77 of the medication delivery manifold 36 into the medication cylinder 40;

During this operation medication piston 46 is actuated to expand the medication reservoir 41 to accommodate the volume of the medication;

When trigger 21 is pulled the hydraulic control valve 32 is then energised closing off the receiving port of the medication control valve 32 and opening up the applicator or needle port of the medication control valve 32. The delivery ports 53, 79 are common ports meaning that when energised or de-energised medication can flow in both directions.

The pneumatic control valve 67 of the pneumatic system 64 then energises allowing a pressurised gas, for example from the from the pressure vessel 64, into the drive cylinder 42 to pressurise and urge the drive piston 48 forward which in turn moves the medication piston 46 forward which reduces the volume of the medication reservoir 41 thereby urging or forces out of the medication cylinder back into the delivery manifold 36.

From the delivery manifold 36, the medication then moves back through the delivery ports 53, 79 in the medication valve 32 to the needle or applicator port 51 of the medication valve 32 which then moves through the medication manifold via a medication delivery path conduit 86 to the applicator tip 23 to deliver the medication to the animal Referring now to FIGS. 8a to 8d, there is shown another example of an apparatus 500 which functions in a similar way to the apparatus 10 as described above. Accordingly, like numerals are used to denote like parts and the focus on the description below are on the features which are different between apparatus 10 and apparatus 500.

Figure 8A:
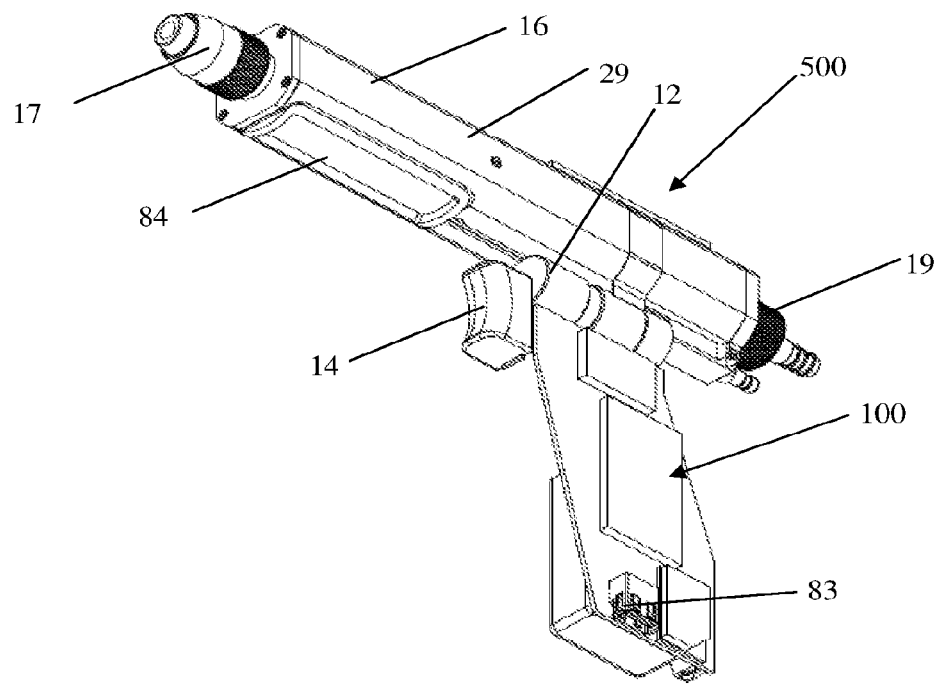
FIG. 8a is an underside perspective view illustrating a second example of the apparatus.
Figure 8B:
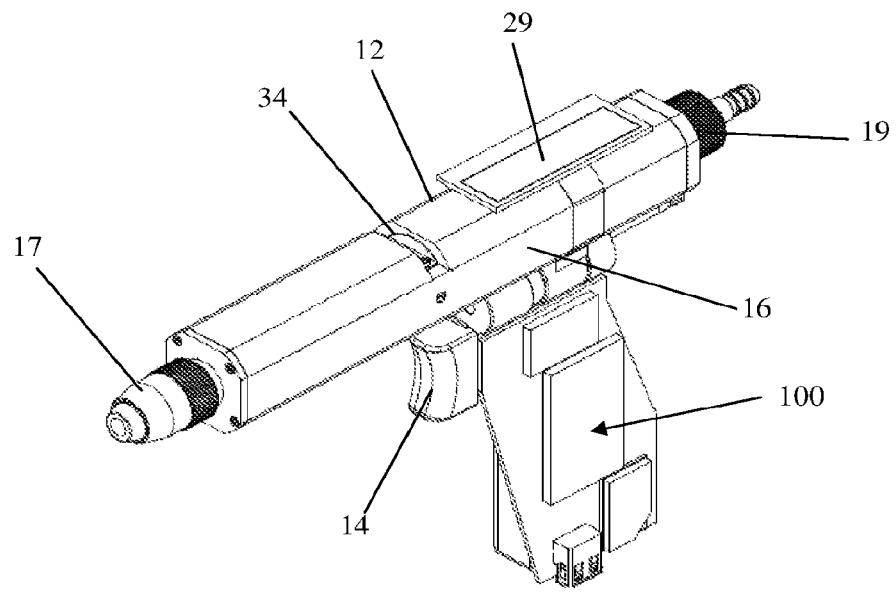
FIG. 8b is a topside perspective view illustrating the second example of the apparatus.

Referring to FIGS. 8a and 8b, the apparatus 500 includes a fluid communication or transmission assembly provided in this example as a delivery assembly 12. The apparatus 500 is preferably hand held and includes a gun shaped body 16 which houses and supports the delivery assembly 12 and an actuator 14, respectively. The body 16 includes a delivery or front end 17 and a rear end 19. The apparatus 500 also includes a display 29 for displaying status and a control system 100 which is configured in a similar way to that of apparatus 10.

This example of the apparatus 500 also includes a detection or identification reader device 84 which is provided in this example as Radio Frequency Identification Device (RFID). The detection device 84 is located on the front or application end 17 of the body 16.

Figure 8C:
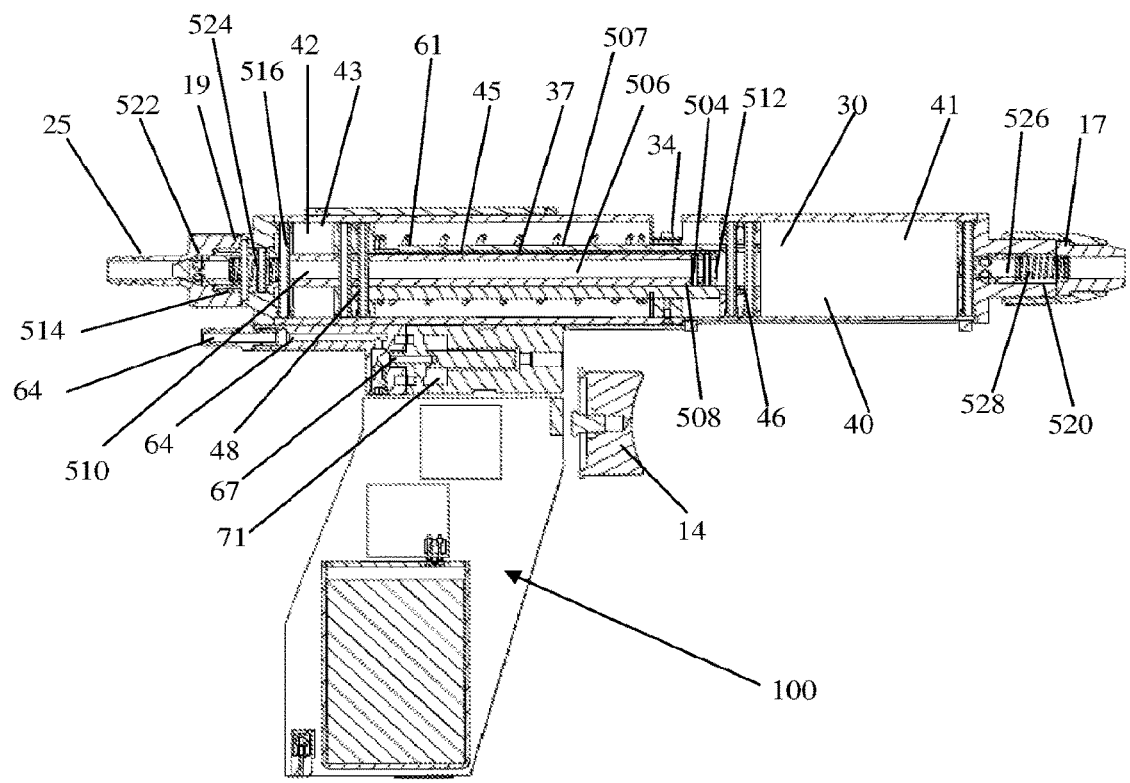
FIG. 8c is a side sectional view of the illustrating the second example of the apparatus.

Referring to FIGS. 8b and 8c, the delivery assembly 12 includes a medication storage arrangement 30 and a drive arrangement 37. The drive arrangement 37 is controlled by the control system 100 to operate the medication storage arrangement 30 so as to receive, store and deliver a pre-determined or select quantity or dose of medication to an animal.

Similarly to the first example of the apparatus 10, the medication storage arrangement 30 includes a medication cylinder 40 which provides a substance reservoir 41 for the temporary storage of medication. The drive arrangement 37 is operatively associated with the medication cylinder 40, in particular, the medication reservoir 41 to draw medication into the reservoir 41 and urge medication out of the reservoir 41. The drive arrangement 37 includes a drive cylinder 42 which provides a drive reservoir 43. The drive cylinder 42 and medication cylinder 40 coupled to or linked to one another by a plunger 37 for likewise control and actuation.

In this example of the apparatus 500, the plunger 37 has a substantially hollow piston rod 504 extending between a first or medication piston 46 and a second or drive piston 48.

The hollow piston rod 504 is dimensioned to receive an internal substance conduit 506 which extends between a substance delivery manifold 514 and the medication reservoir 41. The internal substance conduit 506 is fixed to the body 16 of the apparatus 500 and has a cylindrical shape which is slidably received by the hollow piston rod 504 of the plunger 37. In this arrangement, internal substance conduit 506 and the hollow piston rod 504 function together as a telescopic conduit 507 which is moveable between an extended and retracted condition when the drive arrangement 37 is activated to move the substance reservoir between the expanded and contracted conditions, respectively.

Accordingly, as may be appreciated, in this example, the fluid substance conduit 35 of the first example of the apparatus 10 has been replaced by the telescopic conduit 507. Accordingly, the delivery of the fluid substance to the medication reservoir 43 and the delivery end 17 has been simplified.

The internal substance conduit 506 includes a forward end 508 in communication with medication reservoir 41 and an opposing rear end 510 in communication with the substance delivery manifold 514. The forward end 510 includes a seal 512 in the form of n-rings which provide a sliding seal with the inner surfaces of the moveable hollow piston rod 504 and the rear end 510 includes a further seal 516 between the rear end 510 and the substance delivery manifold 514.

In this example, the apparatus 500 also includes a measurement sensor 34 which is located adjacent to the hollow piston rod 504 intermediate the drive cylinder 42 and the medication cylinder 40. As may be best appreciated by FIG. 8b, the drive cylinder 42 and the medication cylinder 40 are separate sealed units and the measurement sensor 34 is fitted between the sealed units so as to be exposed to and accessible from the external environment.

Figure 8D:
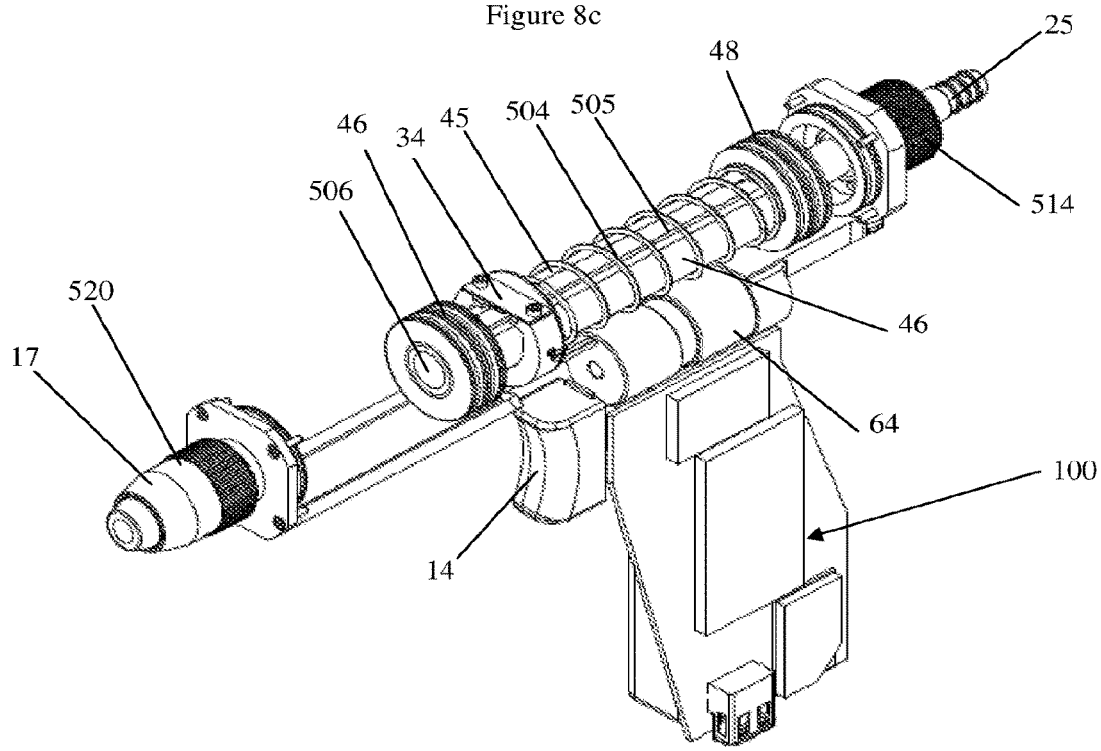
FIG. 8d is a topside perspective view illustrating parts of the second example of the apparatus.

As may be best appreciated from FIG. 8d, the hollow piston rod 504 includes or may be fitted with encoded or sensor portion 45. In this example, the sensor portion 45 is provided in the form of an elongate strip 505 running along a top of the hollow piston rod 504. The measurement sensor 34, which may be in the form a linear encoder, functions with the sensor portion 45 to determine the position of the hollow piston rod 54 which is in turn used to calculate the volume of administered medication as has been described above relation to the first example of the apparatus 10 and is further described below with reference to the operation of the control system 100.

Similar to the first example of the apparatus 10, in this example of the apparatus 500, the drive cylinder 42 is in fluid communication with a pneumatic system 64 via a pneumatic control valve 67 which are configured to provide a controlled delivery and release of pressure to the drive cylinder 40, expanding and contracting the drive reservoir 43 which in turn expands and contracts the substance reservoir 41 allowing for the dispensing of the substance from the delivery end 17.

In this example, the pneumatic system 64 may be connected to a pneumatic power system or energy unit 62 similar to that described for the first example of the apparatus 10, or may simply include a pneumatic fill nozzle or coupling 63 as is shown in FIG. 8c which may be fluidly coupled to an external source of pressurised gas such as a LPG gas bottle or Oxygen bottle. The pneumatic manifold 71 may include a plurality of conduits which are arranged with the control valve 67 to allow the delivery of pressurised air to the drive cylinder 42 in a first delivery state 42 and allow the release of pressurised air from the drive cylinder 42 in a second refill state. The pneumatic manifold 71 includes ports and an exhaust configured in a similar way to that described in relation to the first example of the apparatus 10 and these features are not again detailed here.

The substance delivery manifold 514 includes a delivery valve 522 which is configured to selectively allow the substance to pass from the nozzle 25 into the internal delivery conduit 506. The valve 522 includes spring 524 which biases the valve 522 into an ordinarily closed position. The valve 522 is configured to open under an internal vacuum created when the delivery piston 46 moves the medication reservoir 41 from the evacuated or contracted state to the expanded state. This allows the substance to flow into the medication reservoir 41 via the internal telescopic conduit 507 as the reservoir 41 expands thereby filling the reservoir 41. Once the medication reservoir 41 is filled, the vacuum is reduced or removed, and the valve 522 returns to the ordinarily closed position.

The apparatus 500 also includes a nozzle manifold 520 which include nozzle valve 526 which also includes a spring 528 to bias the valve 526 into an ordinarily closed position. The nozzle valve 526 is arranged in an opposing direction to the delivery valve 522 such that when the nozzle valve 526 is open, the delivery valve 522 is closed. For example, when the medication reservoir 41 is being moved from the evacuated state to the expanded state, the nozzle valve 526 is closed to prevent air entering the medication reservoir 41. However, when mediation is to be delivered by the nozzle, the nozzle valve 526 becomes opened and the delivery valve 522 which allows the substance within the medication reservoir 41 to be delivered to the animal becomes closed.

Similarly to the first example, the hollow piston rod 504 is biased toward the first position, in which the medication reservoir is in the expanded state, by a biasing means, in this example a return spring 61, which is concentrically mounted on the rod 504 within the drive cylinder 42. When the pressurised gas is introduced into the drive cylinder 42, the plunger 37 is moved toward the second position in which the medication reservoir is at least partially contracted. This movement energised the return spring 61. When the pressure is released, the spring 61 urges or forces the plunger 37 back to or toward the first position.

Turning now to the flow and delivery of the fluid substance in more detail, by way of example only, the process for medication flow into and out of the apparatus 500 may function as follows:

Beginning with the medication reservoir 41 in the expanded state with the medication piston 46 located toward the rear end of the medication cylinder 40. It is assumed here that the apparatus 500 has been undergone an initial priming step whereby air is evacuated from the medication reservoir 41 and the medication reservoir 41 is filled with the substance;

When trigger 21 is activated or pulled the pneumatic control valve 67 is moved to a fill position allowing a pressurised gas, for example, gas from the pressure vessel 64, into the drive cylinder 42 to pressurise and urge plunger 37 forward from the first position to toward the second position which in turn moves the medication reservoir 41 toward the contracted state. The pressure inside the medication reservoir 41 thereby opening the nozzle valve 526 and maintaining the delivery nozzle 522 in the ordinarily closed position.

During this movement, the measurement sensor 34 is measuring the distance moved by the hollow plunger rod 504, and the distance measurement is being converted by the control system 100, using a dose calculation algorithm as is further described below, to a volume of substance administered or a dose.

Once the control system determines the pre-determined dose has been reached, the pneumatic control valve 67 is moved to a re-fill position in which an evacuation or exhaust port is opened between the drive cylinder 42 and the external environment. This allows the return spring 61 to move the plunger 37 back to the first position in which the medication reservoir 41 is in the expanded state. During this movement, the delivery nozzle 522 moves to an open position which allows the flow of the substance into the mediation reservoir via the telescopic conduit 507. The nozzle valve 526 moves to a closed position to prevent air entering the medication reservoir 41 and maintains the vacuum. The plunger 37 then reaches its mechanical limits and is retained in the first position until the trigger 21 is next actuated.

As may be appreciated from the above, the second example of the apparatus 500, provides a mechanical configuration which is more compact and has a simpler configuration in comparison to that shown in the first example of the apparatus in 10. Furthermore, the generally linear operation allows for relatively simple control having a feedback control system 100 including the measuring sensor 34 and the pneumatic control 67 which are activated by a user to deliver a pre-determined or select quantity or dose of a substance such as medication as is further described below.

Figure 9:
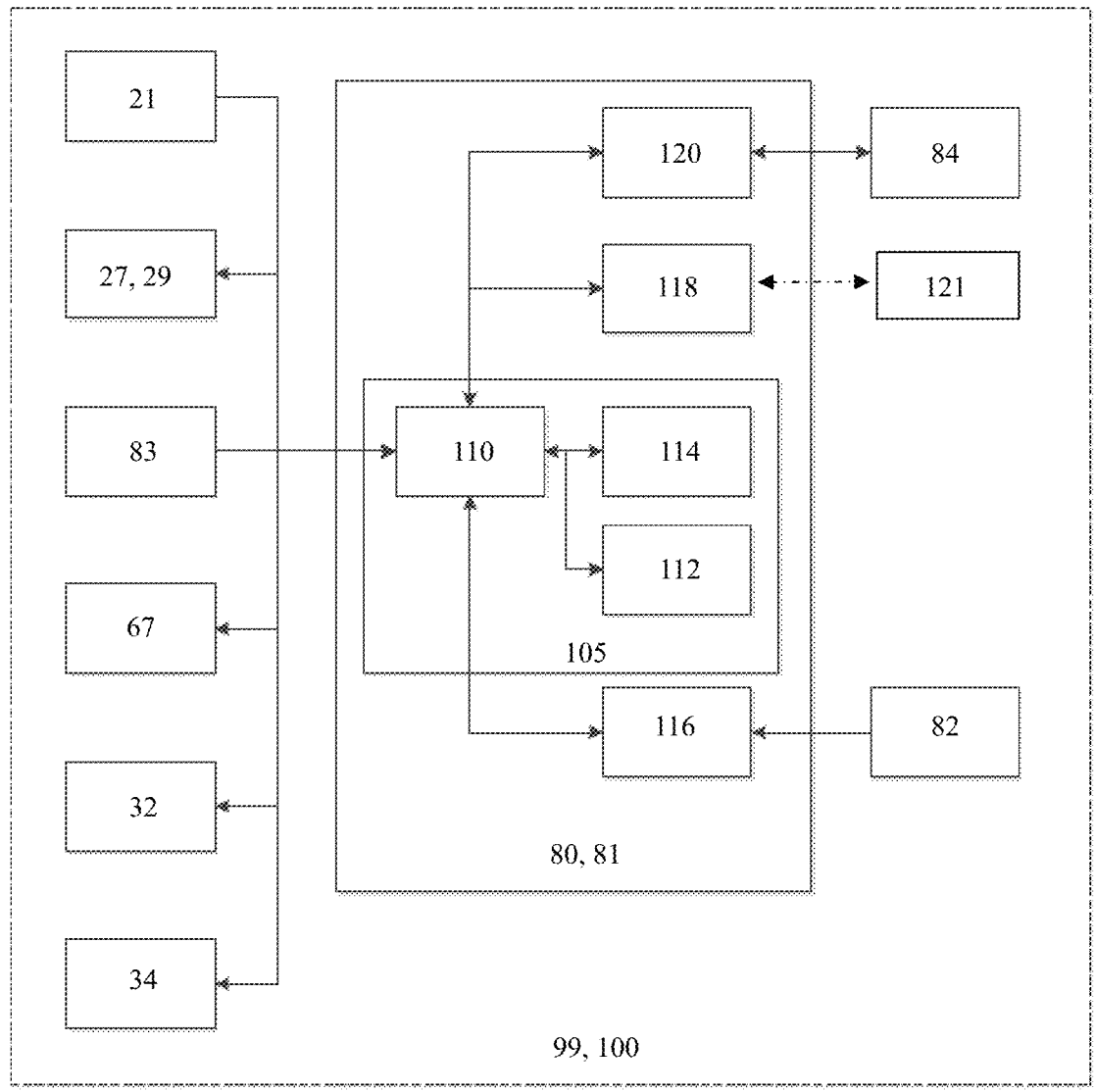
FIG. 9 illustrates a configuration of a control system of the apparatus.

Turning now to the control system 100 more detail. Referring to FIG. 9, the control system including a controller 99 including a processing module 105, a battery controller 116, a wireless communication module 118 and an identification controller or processor 120. The processing module 105 includes a main processor 110, a memory device or system 112 and a watch dog processor 114. The control system 100 in combination with the apparatus 10 may be considered as an overall medication delivery system 101 for the automated delivery and recording of medication administered to an animal.

The control system 100 may be physically supported by and may be connected by the control board assembly 80 includes a printed circuit board assembly (PCB) 81. The PCB 81 includes circuitry to provide the necessary electrical connections, for example, between the processing module 105, battery power supply 82, the wireless communication module 118 and the identification controller or processor 120. The identification controller or processor 120 is in communication with, such as by electrical connection, with the identification device 84.

The control system 100, more specifically the processor 110 of the processing module 105, is operatively connected to or electrically connected to parts of the apparatus 10 including the hydraulic control valve 32, the pneumatic control valve 67, the trigger 21, the sensor 34, the detection device 84, the display 27 and LED 29, and the connection system 83.

Accordingly, the control system 100 is configured to coordinate or control the functionally of the apparatus 10 in response to input from other parts of the control system 100. The control system 100 also monitors the system status such as component health to ensure that there are no faults or errors and the correct function is being carried out.

The memory storage device 112 may be any form suitable memory such as flash, RAM etc. which enables the device to store any required computer readable and executable medium such as software for execution by the processing module 110. For example, the memory storage device 112 may be configured with sufficient storage capacity to storage a copy of an animal identification and medication dose rate database. This allows the apparatus 10 to be used independently of any associated computer or data networks which may be advantageous in farming and remote location applications.

The processing module 105 may include or be formed of a micro-controller or similar controller. The processor 110 may be any suitable computer or mobile device processor capable is operating a computer readable medium such as computer code or software. In this example the processing module 105 is supported or located on the control board 80 which housed within the body 16 of the apparatus 10. However, the processing module 105 may be housed externally to the body 16 of the apparatus 10 and communicated via physical or wireless connection to the body 16 of the apparatus.

The wireless communication module 118 includes a blue tooth or WiFi antenna supported or connected to the board 80 for wireless communication, in particularly data transfer, to and from external remote devices 121 such as remote computer or mobile computing devices. In some example methods of the operation of the apparatus, processing operations and data storage may be conducted via an external computing device 121 which may include or house the controller 99 having the processing module 105 or include a further processing module for processing animal information and calculating dose rates.

Figure 10:
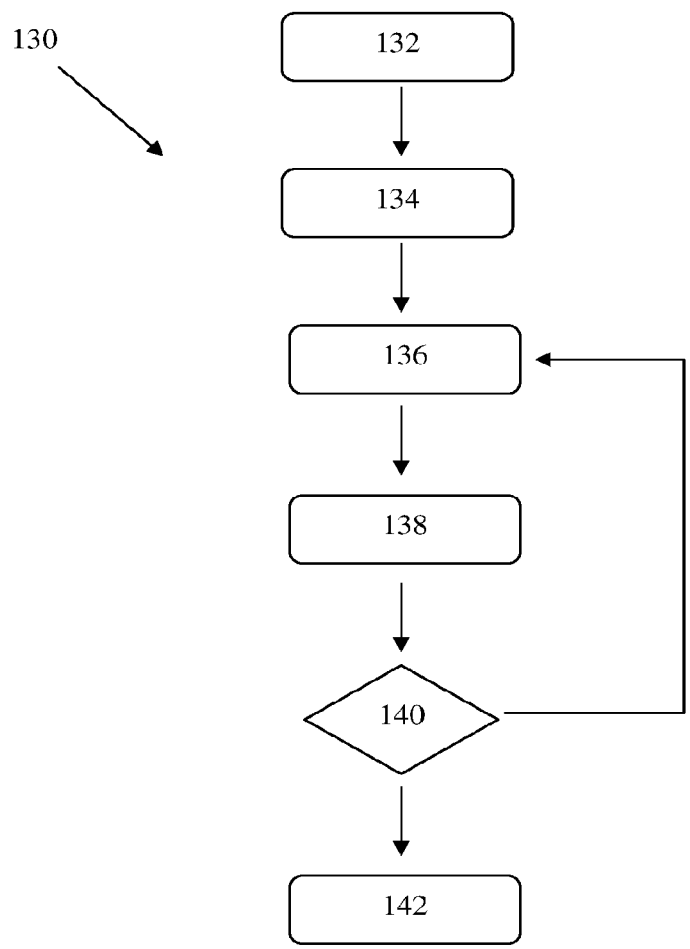
FIG. 10 illustrates an example method.

Referring now to FIG. 10, in a general form of a method or process 130 of operation of the apparatus 10 including the control system 100 is as follows. The steps below are performed in response an external input from an operator and programmed actions of the control system 100. In particular, a machine readable and executable code such as computer software program which forms part of the control system 100 may be used to define the control logic, the sequence of steps and calculations are described below.

The method 130 for delivering a dose of a substance to an animal using a substance delivery system including a delivery assembly 12 operatively associated with the control system 100, may include the steps of: receiving, at step 132 animal information, the animal information may includes at least one of an animal weight data and animal identification data. The information may be received by the identification device 83, the input device 83 or other date input means such as a WiFi or Bluetooth communication unit.

The method then includes a dose determination step 134 where the control system 100, more specifically a controller 99, processes the animal information to provide a determined dose of the substance to be administered to the animal. This may involve a dose rate determination algorithm to be executed which is further described with reference to FIG. 11 below. The delivery assembly 12 is then activated, via the control system 100, at activation and delivery step 136 delivery system discharges the determined dose of the substance to the animal. A measurement step 138 is then undertaken by the control system 100 using the measurement sensor 34 to determine if the delivered dose is equal to the determined dose. The control system 100 then performs a comparison step 140 to determine if the delivered dose equals the determined dose. If the delivered dose equals determined dose the control system 100 then conducts deactivation step 140 whereby the delivery assembly 12 is deactivated to stop the delivery of the substance.

Figure 11:
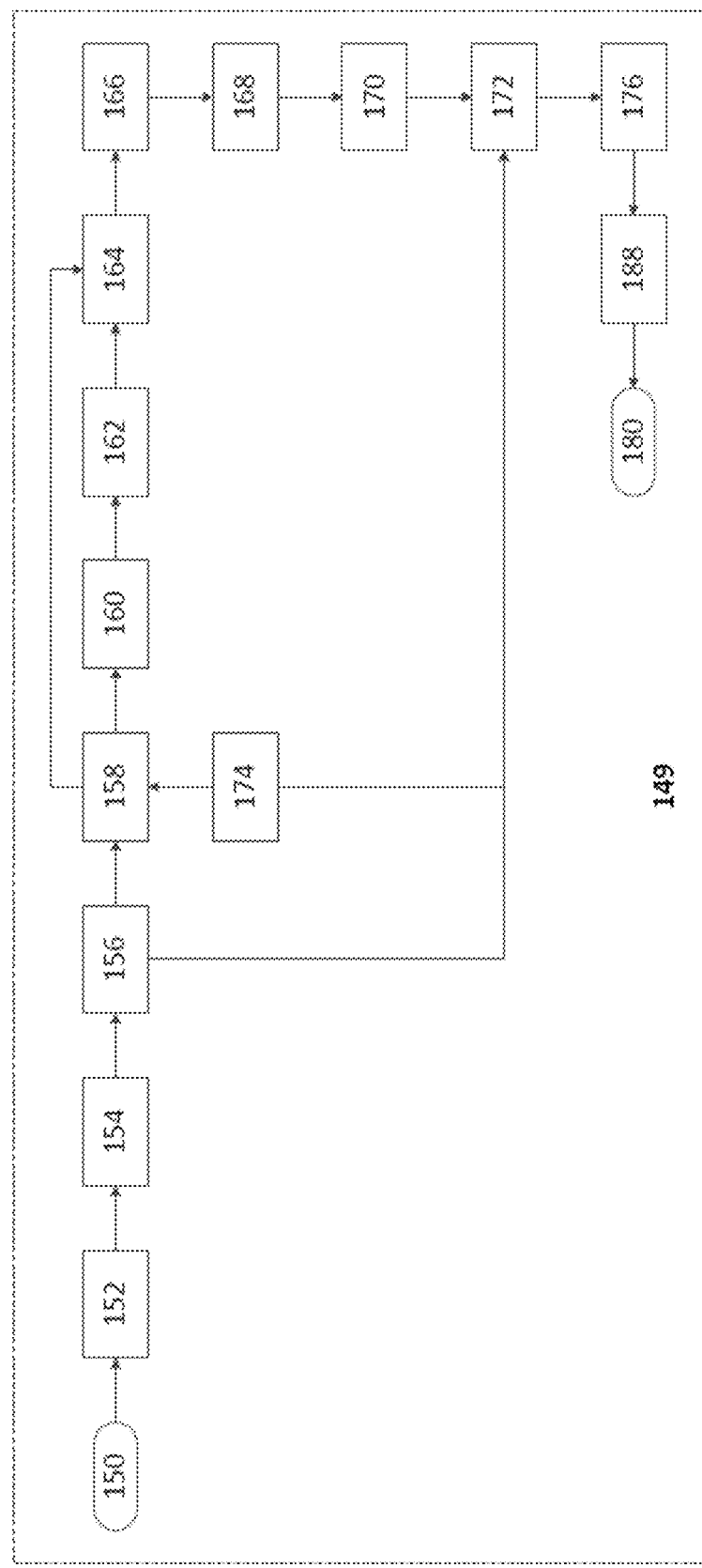
FIG. 11 illustrates another example of method for the operation of the apparatus.

Referring now to FIG. 11, following on in more detail, a method or process 149 of operation of the apparatus 10 including the control system 100 is as follows. The steps below are performed in response an external input from an operator and programmed actions of the control system 100. In particular, a machine readable and executable code such as computer software program which forms part of the control system 100 may be used to define the control logic, the sequence of steps and calculations are described below.

Beginning with step 150, the operator actuates or provides an external input to the actuator 14, more specifically the trigger 21, of the apparatus 10 which sends a signal to the detection device 84 via the control system 100. This initiates an identification step 152 in which, for example, an RFID reader of the apparatus 10 reads an RFID tag of an animal to identify the particular animal.

The control system 100 then initiates an animal identification lookup step 154 wherein the identification of the animal is matched to a pre-defined database or stored information located in the memory 112 of the control system 100. This stored information may be pre-loaded or stored in the memory 122 and may include animal parameters such as weight, height, age, sex and/or other similar information.

On matching the animal identification with the stored information the control system 100 retrieves the animal parameters at an animal parameters lookup step. The animal parameters may include the animal weight, type and age as well as related information which is used to calculate the dose rate.

The dose rate is calculated at a dose rate calculation or processing step 158 using animal parameters 156 and medication parameters 174. The medication parameters 174 may include information such as type of medication and dose rate lookup tables, for example dose in ml/kg for selected medications, which are utilised in the dose rate calculation. The medication parameters 174 may be pre-loaded or stored in the memory 112 and accessed by the processor 110.

The dose rate algorithm as is further detailed below in Tables 1 and 2. The calculation may be undertaken in the processing module 105 by the execution of a computer readable medium such as computer code which includes the algorithm. The computer code may be stored on the memory device 112 and accessed by the processor 110 when required to execute the code.

TABLE 1

Parameters for the Dose Rate Algorithm

| Parameter | Unit of Measure | Abbreviation | Example |
|---|---|---|---|
| Weight | kg | W | 20 kg |
| Medication Rate | ml/kg | MEDR | 0.5 ml |
| Calculated Rate | ml | CALR | |
| Medication Cylinder Volume | mm2 | V | |
| Medication Cylinder Length | mm | L | 1 mm |
| Medication Cylinder Radius | mm | r | 7 mm |
| Dose Rate | mm | DOSR | |
| Device Rate | ml/mm2 | DEVR | |

*It is noted that the Medication Cylinder Length in the calculations is determined on a per mm basis. The actual length of the medication cylinder may be, for example, between 50 mm and 200 mm.

TABLE 2

Algorithms used to calculate the dose required

| Algorithm | Example |
|---|---|
| $V = \pi r^2 \times L$ | $V = \pi \times 7^2 \times 1$ |
| | $V = 153.9379$ |
| DEVR = V ÷ 1000 | DEVR = 153.9379 ÷ 1000 |
| CALR = W × MEDR | CALR = 20 × 0.5 |
| | CALR = 10 |
| DOSR = CALR ÷ DEVR | DOSR = 10 ÷ 0.1539 |
| | DOSR = 64.9773 |

Accordingly, from the above it may be appreciated that based on an identified animal weight, provided at the animal parameters look up step 156 and the medication parameters provided at the medication parameters look up step 174, the control system 100 calculates the required dose rate.

In this example, the dose rate, DOSR, which is a linear movement required by drive system 49, more specifically the plunger 39, to deliver the required amount of medication. In this example, the required amount is 0.5 ml/kg for a 20 kg animal which is 10 ml which result in a DOSR of 64.9773 mm.

Accordingly, following the dose rate calculation step 158 the drive system 49 is activated at the drive activation step 160 by the control system 100. This activation requires the activation on the pneumatic system 64 and in particular the activation of the pneumatic valve 67 to allow flow of pressurised gas into the drive cylinder 42 thereby urging and moving the plunger 39.

Immediately after or during the drive activation step 160, a medication system activation step 162 is performed. The medication system activation step 162 includes activating the medication and delivery arrangement 30 to administer the medication to the animal. More specifically, this includes activating the hydraulic flow control valve 32 (for the first example of the apparatus 10) so as to allow the flow of fluid, in this example medication, from the medication cylinder 40 to the applicator 23.

The sensor 34 then performers a measuring step 164 in which sensor 34 measures the linear movement of the plunger 39. The sensor 34 is in communication with the processing module 105 and when the required dose rate is reach, in this example 64.9773 mm, the drive system 49 is deactivated by the control system 100 at a drive system deactivation step 168. This step required that the pneumatic valve 67 closes the port to the drive cylinder 42 and opens the air exhaust port 88. The spring 61 then urges the plunger 39 back to the first position.

The medication and delivery arrangement 30 will also be deactivated by the control system 100 at medication system deactivation step 170 and the medication delivery will be stopped by deactivating the hydraulic control valve 32 which in turn closes or shuts the applicator port 51 of the delivery manifold 36. This step may also involve opening the delivery port 53 such that further medication may be drawn from the medication fill tube 35 into the medication reservoir 41 as the spring 61 urges the plunger 39 back to the first position in the drive system deactivation step 168.

A recording step 172 is then preformed whereby the animal dose calculated in step 158, the medication parameters which were located in step 174 and the animal parameters located in step 156 are written to an information file by the processing module 104. The information file may be, for example, a database file or similar. The information file is then communicated or recorded to the memory device 112 at storage step 176.

Once the recording step 172 and the storage step 176 are complete, the control system 100 issues a process complete command at step 176. This may involve the control system providing a notification signal which may generate a symbol on the display 29 or the LED light 27 to become activated. This informs the user that the apparatus is ready to identify and scan the next animal at step 180. After step 180 steps 150 to 180 may be performed again on numerous animals.

Figure 12:
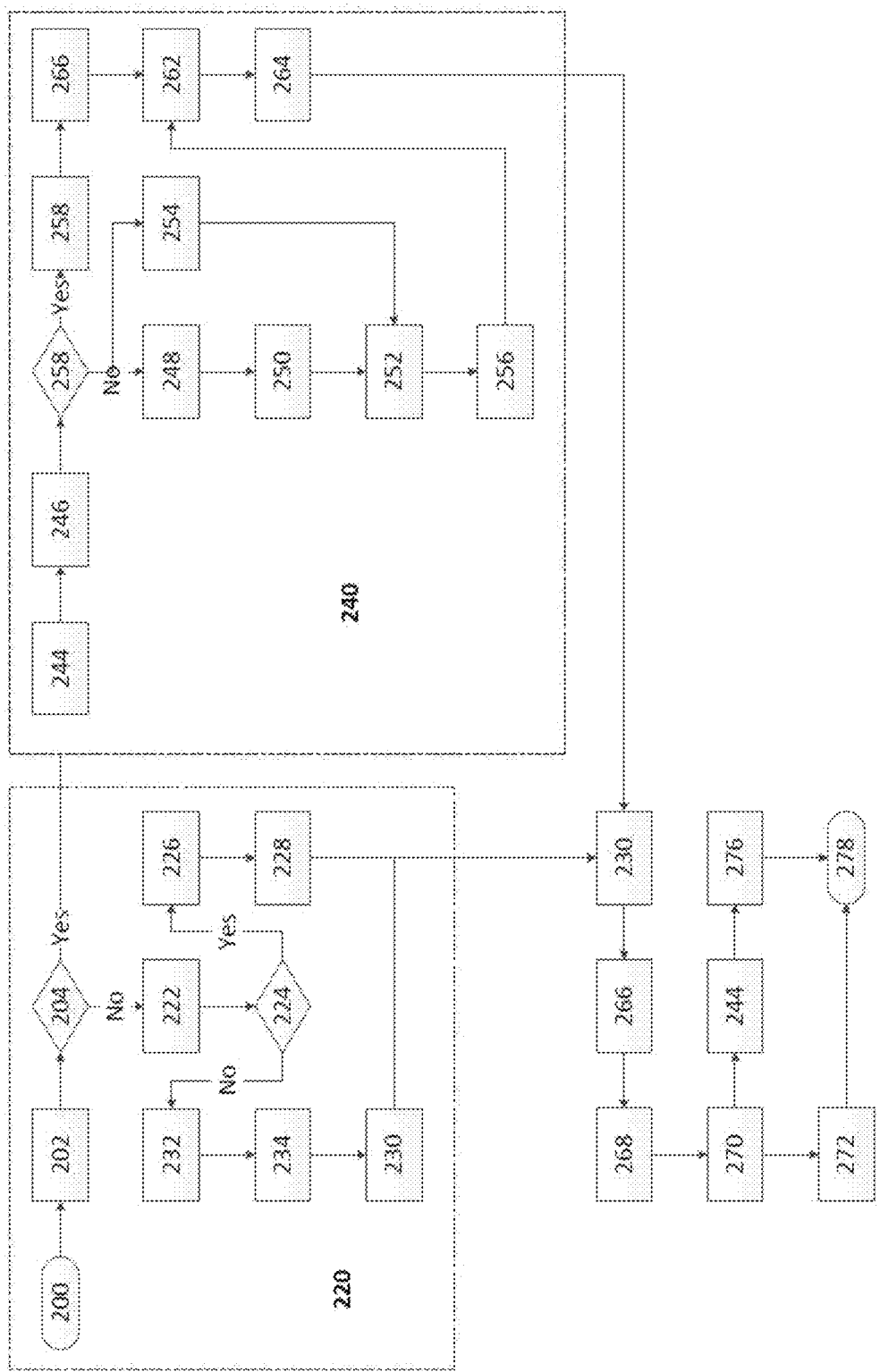
FIG. 12 illustrates another example of method steps for the operation of the device.

Referring now to FIG. 12, another example of the method or process 199 is described. Beginning with step 200, the operator actuates or provides an external input to the actuator 14, more specifically the trigger 21, of the apparatus 10 which sends a signal to the detection device 84 via the control system 100. This initiates an identification step 202 in which, for example, the RFID reader of the apparatus 10 reads an RFID tag of an animal to identify the particular animal. An animal identification code is then generated.

A processing selection step 204 may then be undertaken whereby the control system 100 determines if the dose rate calculation will be undertaken internally of the apparatus 10 or externally of the apparatus 10. This step depends on whether the apparatus 10 has been configured to have an integral processing module 105 or is required to access an external processor.

If the apparatus 10 has an integral processing module 105, then internal processing and calculating steps 220 are undertaken. However, if the apparatus 10 has an external processing module 105 then external processing and calculation steps 240 are undertaken.

In the internal processing and calculating steps 220, the control system 100 firstly undertakes a memory checking step 222 to determine if the memory storage device 83 has a stored dose rate list.

If the memory storage device 83 has a stored dose rate list, then a dose rate search step 226 is initiated in which the control system 100 searches the dose rate list. The control system 100 then undertakes a dose rate selection step 228 to select a dose rate based on matching or associating the animal identified at step 202 with a particular dose from the dose rate list.

The dose rate is then converted in the processing module 105 by a dose rate algorithm in a dose rate calculation step 236 which calculates the required linear movement of the connecting rod 44 and hence the movement of the plunger 39 required to delivery the required dose of medication to the animal. The dose rate calculation algorithm and parameters are shown in Tables 1 and 2 above.

If there is no dose rate list stored the memory device, the apparatus 10 may undertake a separate series of steps 232 to 236 in which the dose rate may be manually configured or may undertake calculations based on the animal weight, bread and age to determine the dose rate. For example, the apparatus 10 may be configured 232, animal parameters 234 may be entered, such as weight, bread and age. A calculation step 236 is then undertaken and the dose rate is communicated to the medication delivery system 30 at step 230.

If the control system 100 determines that an external calculation is required then external steps 240 are undertaken. These steps include a communication step 242 to communicate or transmit with a receiving module (not shown) that may include external part of the control system 100, in particular, a software programme.

The incoming communication 242 is received by the software system 246 which then determines if there is a stored dose rate list in step 246. If there is no dose rate list, the programme initiates a database search of the animal search database 248 and the medication database 254.

Animal parameters 234 may be entered, such as weight, bread and age or identified from the animal identified in step 202. A dose rate calculation step 252 is then undertaken and the calculated dose rate 256 is communication by a sending 262 and a transmission step 262 to the medication delivery system 230. Again, this calculates the required linear movement of the connecting rod 44 and hence the movement of the plunger 39 required to delivery the required dose of medication to the animal. The dose rate calculation algorithm and parameters are shown in Tables 1 and 2 above.

If at step 246 the dose rate list is present, then a dose rate search step 258 is initiated in which the control system 100 and/or associated software searches the dose rate list. The control system 100 then undertakes a dose rate selection step 260 to select a dose rate based on matching or associating the animal identification code 203 with the a particular dose from the dose rate list. The calculated dose rate 260 is communicated to the apparatus 10 by a sending and a transmission step 262 to the medication delivery system 30.

The operator then performs a substance or medication delivery step 268 whereby the animal is medicated. This step may include inserting the application tip 23 into the animal to inject the animal with the substance or medication or this step may include spraying or pouring the medication into the mouth or other orifice of the animal as required.

Once the or as the animal is being medicated the control system 100 initiates an animal record medication step 276 in which the animal identification code 203, the dose rate, and other information such as time and date are recorded on the memory device 83.

If an external record is required, the communication transmission step 274 is undertaken and the medication record is received and stored at a recording and storage step 276 whereby the record stored on an external memory device. If the internal memory is used, an internal record step 272 is undertaken whereby the record stored on internal memory device which may then be later accessed or downloaded.

Figure 13:
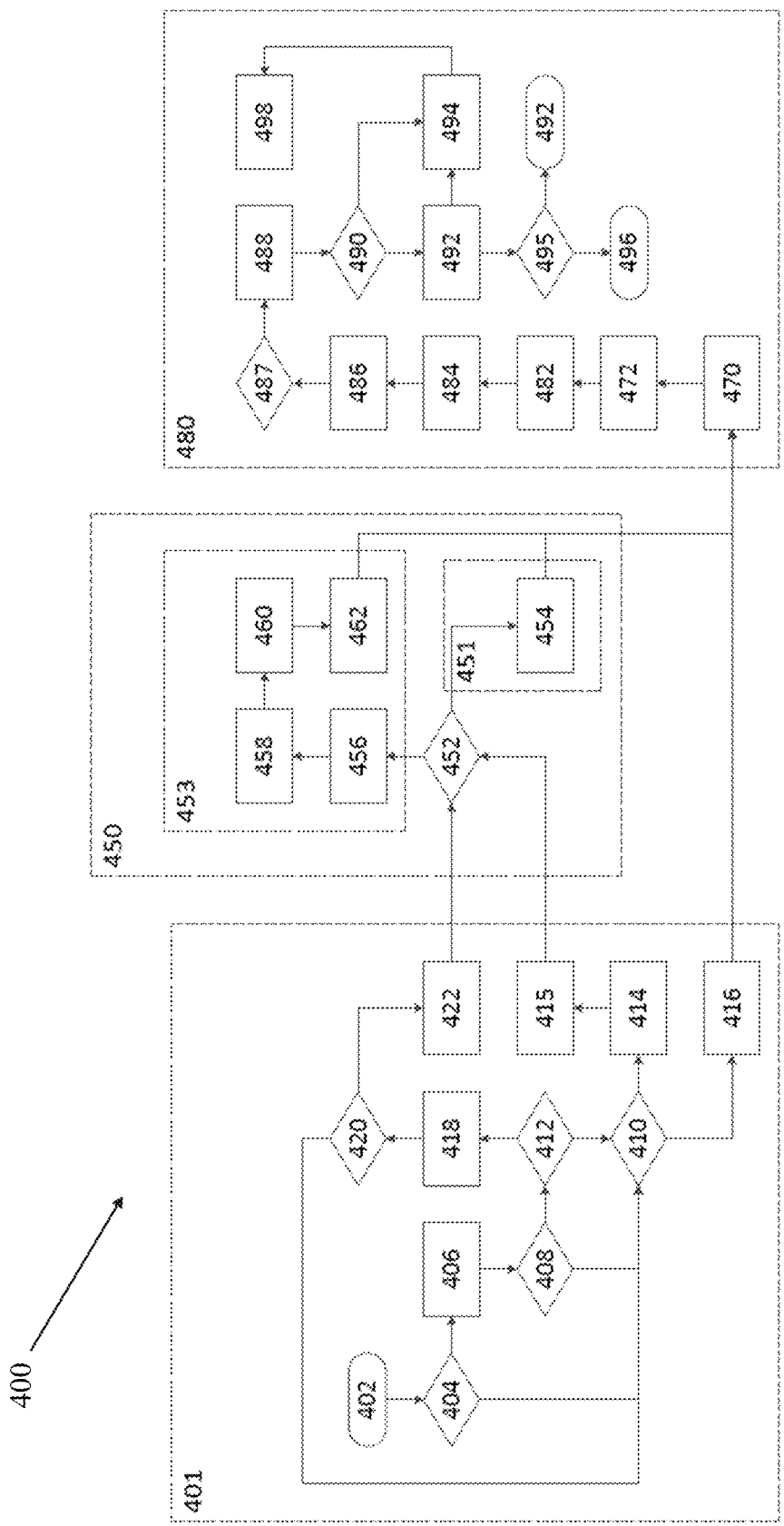
FIG. 13 illustrates yet another example of method steps for the operation of the device.

Referring now to FIG. 13, there is provided another example of the method or process 400 is described. In this example, the apparatus 10, 500 may be used without the scanning of an animal identification and may take direct input of animal information such as animal weight from a user input (such as via the display 29) or via the connection system 83 such as by receiving information via a USB cable or via WiFi system using communication module 120. The steps below are performed in response an external input from an operator and programmed actions of the control system 100. In particular, a machine readable and executable code such as computer software program which forms part of the control system 100 may be used to define the control logic, the sequence of steps and the calculations as are described below.

Beginning with step 402, the operator actuates or provides an external input to the actuator 14, more specifically the trigger 21, of the apparatus 10, 500. At step 404, the control system 100 then determines if the apparatus 10, 500 is in "ID mode" or "Live Input mode". The control system 100 may be preconfigured in these modes utilising a user interface provided on the display 29. In "ID mode" the control system 100 initiates an identification step 406 and in "Live Input mode" the control system 100 initiates a live input step 410.

In more detail, if the control system 100 determines that the apparatus 10, 500 is in "ID mode", the control system 100 initiates identification step 406 whereby the control system 100 sends a signal to the detection device 84. This initiates an, for example, the RFID reader of the apparatus 10, 500 reads an RFID tag of an animal to identify the particular animal.

At step 408, the control system 100 undertakes an identification checking step to determine if there is identification available, for example, if the identification provides a recognisable an animal identification code. If there is no identification available the control system 100 provides an error to the display 29. If there is identification available, the control system 100 undertakes a determination step 412 in which the control system 100 determines if there is a stored dose list. This may be stored on an internal or external memory device. The determination step 412 may also include providing a prompt to a user via the display 29 where the user may select to use a stored dose list or use a live input at step 410.

At step 410, the control system 100 determines if there is a live input available. The live input may include animal information, in particular, animal weight information which is directly inputted into the apparatus 10, 500. If there is live input available, the control system 100 then undertakes step 414 in which the control system seeks to obtain the live measurement. The live animal information may an animal weight generated from a set of weigh scales or the like.

At step 415, the live measurement may be obtained or retrieved by the control system 100 from a user input or from an external animal weight measuring device or apparatus such as the set weigh scales. Once the live information, such as weight information, is retrieved the live information the control system 100 initiates the dose calculation routine at step 450. If there is no live input available at step 410 the control system 100 adopts a default dose at step 416 which is ultimately used to dose the animal at step 470.

Returning now to determination step 412, if the control system 100 uses the dose list then the control system 100 initiates a database look up and retrieval step 418. During this step the control system 100 compares the identification code or signal received with a stored database. The database may be a local or a remote database.

At step 420, the control system 100 determines if the ID matches any of the database records. If there is no database record, an error message may be provided to the user via the display 29. If the database record is available then the control system 100 conducts a parameters and retrieval operation step 422 to retrieve animal information which may include information such as the animal ID, animal weight, the animal medication as well as dose rate parameters. Once the animal information has been retrieved, the control system then initiates the dose calculation routine 450.

In the dose calculation routine 450, a processing selection step 452 is undertaken whereby the control system 100 determines if the dose rate calculation will be undertaken internally of the apparatus 10, 500 or externally of the apparatus 10, 500. This step depends on whether the apparatus 10, 500 has been configured to have an integral processing module 105 or is required to access an external processor for the dose rate calculations These steps and calculations are similar to those described in relationto internal processing and calculating steps 220 and the external processing and calculation steps 240 as described above.

If the control system 100 determines that an internal calculation is to be undertaken, the internal calculation step 454 is undertaken in which the dose rate is calculated based on the animal information, such as weight. The details of the calculation are not again provided here and the calculations conducted are similar to that described in relation to processing step 158 using animal parameters 156, medication parameters 174 and as set out in Table 1 and 2.

Similarly, if at step 452 the control system 100 determines that external processing is required, then the control system 100 undertakes a communication step 456 where the animal information is transmitted to an external device such as an external computing device. At step 460, the external computing device undertakes the dose rate calculation. Again the details of the calculation are not again provided here and the calculations conducted are similar to that described in relation to processing step 158 using animal parameters 156, medication parameters 174 and as set out in Table 1 and 2. The calculated dose rate is then transmitted from the external computing device to control system 100 which initiates the delivery system 12 at step 470 to delivery the determined dose to the animal.

Accordingly, following the receipt of the dose rate at step 470 the delivery assembly 12 including the drive system 49 is activated at the drive activation step 472 by the control system 100. This activation requires the activation on the pneumatic system 64 and in particular the activation of the pneumatic valve 67 to allow flow of pressurised gas into the drive cylinder 42 thereby urging and moving the plunger 39.

Immediately after or during the drive activation step 472, the measurement unit sensor 34 is also activated at measurement unit sensor activation step 482. The measuring unit 34 then undertakes a measuring step 484 in which sensor 34 continuously measures the linear movement of the plunger 39. The sensor 34 is in communication with the processing module 105.

At step 486, the control system 100, more specifically the processing module 105 monitors the output from the sensor 34 and the processing module 105 then undertakes a delivered dose determination step 487 in which the processing module 105 determines the delivered dosed. The delivered dose is calculated by the distance moved by the lengthwise of travel of the plunger 37 and equating this movement to the volume of substance delivered using the dose rate algorithm as described above. If the required dose has not been reached the control system 100 continues to operate the delivery system. The processing module 105 continues to compare the delivered dose rate to the required calculated dose rate.

When the required dose rate is reach, the delivery assembly 12 including the drive system 49 is deactivated by the control system 100 at a drive system deactivation step 488. This step requires that the pneumatic valve 67 closes the port to the drive cylinder 42 and opens the air exhaust port 88. The spring 61 then urges the plunger 39 back to the first position. Movement of the plunger 39 back to the first position may refill the medication reservoir 41 as have been described in detail above.

At step 490, the control system 100 determines of the animal information includes any identification determined at step 406 and 408. If the identification has been used, a recording step 492 is then preformed. However, of there no identification has been used, then the control system 100 complete the routine at dose deliver completion step 494 and undertakes an apparatus reset step 498 whereby the apparatus is reset and/or prepared for next use.

A recording step 492 is then preformed whereby animal and dose information, including the animal dose calculated in routine 450, the medication parameters and the animal parameters, are written to an information file by the processing module 105. The information file may be, for example, a database file or similar. The method provides for two recording options at record options selection step 495, the first option is an external recording step 496 whereby the control system 100 communicates the animal and dose information to an external storage device or system. This may be for example an external computing device, an external storage device or an internet or network accessible cloud based storage medium. The second option it is record the animal and dose information internally of the apparatus 10, 500 for example within the memory device 112 at internal storage step 497.

Once the recording step 492 and the storage step 495 are complete, the control system 100 issues a process complete command at dose deliver complete step 494. This may involve the control system providing a notification signal which may generate a symbol on the display 29 or the LED light 27 to become activated. This informs the user that the apparatus is ready to identify and scan the next animal at step 180. After step 498 the device is reset and the method steps 402 to 498 may be performed again on numerous animals.

As may be appreciated from the above, the apparatus, system and methods provides an automated way to administer a dose of medication to an animal. The apparatus is able to scan an animal to identify the animal, calculate or lookup the dose of medication required for a particular animal, delivery or administer that dose the animal and record the given dose for the particular animal.

Accordingly, the above described the apparatus, system and methods advantageously allow the dose of medication to be matched to the weight of the animal to ensure the animal is correctly and quickly medicated. Furthermore, the apparatus, system and methods advantageously provide for the recording of which animal has been medicated and the dose of medication which has been administered.

It is also noted that the above described the apparatus, system and methods have been primarily described in relation to the delivery of a fluid substance to an animal. However, the apparatus, system and method may also be readily adapted to receive a fluid substance such a blood from an animal. This may be achieved by reversing the operation of delivery assembly, in particular, re-configuration of the hydraulic control valve. The sequence of operation in the control system may be required to be modified.

The term animal within this specification is intended to include all manner of living creatures to which substances such as medication are applied or administered. Accordingly, whilst examples have been provided in relation to livestock such as sheep, cattle, horses and goats. An animal may also include humans, domestic pets, aquatic animals such as fish and the like.

The term substance is intended to include any substance that may be administered to an animal. The substances may be in the form of a medication such as a vaccine or antibiotics, vitamins or similar substance. The substance may be a liquid, a liquid containing solids, a gas or a combination of these.

The reference in this specification to any known matter or any prior publication is not, and should not be taken to be, an acknowledgment or admission or suggestion that the known matter or prior art publication forms part of the common general knowledge in the field to which this specification relates.

While specific examples of the invention have been described, it will be understood that the invention extends to alternative combinations of the features disclosed or evident from the disclosure provided herein.

Many and various modifications will be apparent to those skilled in the art without departing from the scope of the invention disclosed or evident from the disclosure provided herein.

The invention claimed is:

1. An apparatus for delivering a dose of fluid substance to an animal, the apparatus comprising:
    a hand holdable body including a trigger on a handle of the body;
    a delivery assembly carried by the body adapted to deliver the fluid substance;
    a controller carried by the body in operative communication between the trigger and the delivery assembly such that the delivery assembly is operative by the trigger via the controller; and
    an input device carried by the body in communication with the controller to provide animal information to the controller such that the controller is able to determine a dose rate signal indicative of the dose to be delivered to the animal;
    wherein the delivery assembly includes a plunger slidably received by a substance cylinder;
    a power unit;
    a drive arrangement powered by the power unit to move the plunger within the substance cylinder between a first position and a second position, said drive arrangement being a pneumatic drive arrangement; and
    a sensor arranged to measure the position of the plunger continuously between the first and second positions to provide a measured dose rate signal; and
    wherein the controller is configured such that upon actuation of the trigger, the controller operates the drive arrangement and initiates movement of the plunger between the first and second positions to deliver the dose while continuously comparing the measured dose rate signal and the dose rate signal, the controller deactivating the drive arrangement when the measured dose rate signal is about equal to the dose rate signal so as to deliver the dose to the animal.

2. The apparatus according to claim 1, wherein the input device is provided in the form of an identification device operatively associated with the controller, the identification device being configured to provide identity information for the animal.

3. The apparatus according to claim 2, wherein the identification device is one of a radio frequency identification device and an optical scanner.

4. The apparatus according to claim 2, wherein the identification device is a radio frequency identification device having an antenna carried by a forward end of the hand held body.

5. The apparatus according to claim 4, wherein the antenna is recessed into the hand held body at an underside of the forward end.

6. The apparatus according to claim 1, wherein the plunger includes a head received by the substance cylinder and a rod coupled to the drive arrangement, and wherein the rod includes a sensor readable section configured such that the sensor is able to determine the position of the rod relative to the sensor.

7. The apparatus according to claim 1, wherein the animal information includes at least one of animal identification, animal weight and animal age.

8. The apparatus according to claim 7, wherein the controller is configured to calculate the dose based on the animal information and medication information storable in memory in communication with the controller.

9. The apparatus according to claim 8, wherein the medication information includes medication type and associated dose rates.

10. The apparatus according to claim 9, wherein the controller is configured to record in memory the animal information including an animal identification indicative of an identified animal as well as the medication information, a measured dose based on the measured dose rate signal and the calculated dose associated with the identified animal.

11. The apparatus according to claim 1, wherein the hand holdable body carries a communication device configured to communicate data between the controller and an external computer system.

12. The apparatus according to claim 1, wherein the hand holdable body carries display device in communication with the controller, the display being configured by the controller to display a status of the apparatus to the user.

13. A system for discharging a dose of a fluid substance to an animal, the system including:
- a hand holdable body including a trigger carried by a handle for the body and a delivery assembly carried by the body configured to deliver the dose to the animal;
- wherein the delivery assembly includes a plunger slidably received by a substance cylinder,
- a power unit;
- a drive arrangement powered by the power unit to move the plunger within the substance cylinder between a first position and a second position and a sensor arranged to measure the position of the plunger continuously between the first and second positions to provide a measured dose rate signal, said drive arrangement using pneumatic force to move the plunger;
- a control system including a controller in operative communication between the trigger and the delivery assembly such that the delivery assembly is operative by the trigger via the controller;
- an input device in communication with the controller to provide animal information to the controller such that the control system is able to determine a dose rate signal indicative of the dose to be delivered to the animal;
- wherein the control system is configured such that upon actuation of the trigger the controller operates the drive arrangement and initiates movement the plunger between the first and second positions to deliver the dose whilst continuously comparing the measured dose rate signal and the dose rate signal, the controller deactivating the drive arrangement when the measured dose rate signal is about equal to the dose rate signal so as to deliver the dose to the animal.

* * * * *